(12) United States Patent
Walters et al.

(10) Patent No.: US 6,555,028 B2
(45) Date of Patent: *Apr. 29, 2003

(54) POLYMERIC MATRIX COMPATIBILIZED NAPHTHOPYRANS

(75) Inventors: Robert W. Walters, Export, PA (US); Barry Van Gemert, Murrysville, PA (US)

(73) Assignee: Transitions Optical, Inc., Pinellas Park, FL (US)

(*) Notice: Subject to any disclaimer, the term of this patent is extended or adjusted under 35 U.S.C. 154(b) by 63 days.

This patent is subject to a terminal disclaimer.

(21) Appl. No.: 09/828,260

(22) Filed: Apr. 6, 2001

(65) Prior Publication Data

US 2001/0025948 A1 Oct. 4, 2001

Related U.S. Application Data

(63) Continuation-in-part of application No. 09/532,978, filed on Mar. 22, 2000, now abandoned, which is a continuation-in-part of application No. 09/526,232, filed on Mar. 15, 2000, now abandoned, which is a continuation-in-part of application No. 09/437,982, filed on Nov. 10, 1999, now Pat. No. 6,113,814, which is a continuation-in-part of application No. 09/151,911, filed on Sep. 11, 1998, now abandoned.

(51) Int. Cl.$^7$ .......................... G02B 5/23; C07D 311/92; G02C 7/10

(52) U.S. Cl. .......................... 252/586; 549/389; 549/382; 549/331; 549/362; 549/58; 549/60; 546/256; 546/280.4; 546/281.1; 546/282.7; 546/277.4; 546/282.4; 548/454; 524/110; 525/279; 525/403; 351/163

(58) Field of Search .................... 252/586; 549/389, 549/331, 362, 382, 58, 60; 546/256, 280.4, 281.1, 282.7, 277.4, 282.4; 548/454; 524/110; 525/279, 403; 351/163

(56) References Cited

U.S. PATENT DOCUMENTS

| | | | |
|---|---|---|---|
| 4,719,296 A | 1/1988 | Irie et al. | 544/71 |
| 4,929,693 A | 5/1990 | Akashi et al. | 526/259 |
| 5,166,345 A | 11/1992 | Akashi et al. | 544/71 |
| 5,236,958 A | 8/1993 | Miyashita | 518/121 |

(List continued on next page.)

FOREIGN PATENT DOCUMENTS

| | | | |
|---|---|---|---|
| DE | 199 02 771 A1 | 12/1999 | |
| EP | 875509 A1 | 11/1998 | |
| JP | 3-91578 | 4/1991 | |
| JP | 3-100091 | 4/1991 | |
| WO | WO 96/01884 | 1/1996 | |
| WO | WO 97/05213 | 2/1997 | |
| WO | WO 98/04937 | 2/1998 | |
| WO | 00/15629 | 3/2000 | C07D/311/92 |
| WO | WO 01/09645 A1 | 2/2001 | |

OTHER PUBLICATIONS

Bradshaw, J.S., et al., "Synthesis of Macrocyclic Acetals Containing Lipophilic Substituents", Tetrahedron, vol. 43, No. 19, pp. 4271–4276, 1987.
Organic Synthesis, vol. 31, pp. 90–92, John Wiley & Sons, Inc., New York, 1951.
Ullmann's Encyclopedia of Industrial Chemistry, "Polymerization Processes", vol. A21, Fifth, Completely Revised Edition, pp. 305–306, 1992.
Derwent Abstract, JP 5098252, Apr. 20, 1993.
Derwent Abstract, JP 8176139, Jul. 9, 1996.

*Primary Examiner*—Philip Tucker
(74) *Attorney, Agent, or Firm*—Frank P. Mallak

(57) ABSTRACT

Described are polymeric matrix compatibilized naphthopyran compounds, examples of which are certain 2H-naphtho[1,2-b]pyrans, 3H-naphtho[2,1-b]pyrans and indeno[2,1-f]naphtho[1,2-b]pyrans each having at least one substituent containing terminal and/or pendant groups selected from hydroxyl, carboxyl, sulfo, sulfono, (meth)acryloxy, 2-(methacryloxy)ethylcarbamyl, epoxy or a mixture thereof. Specific substituents are also present on the naphtho, indeno and/or pyrano portions of the compounds. These compounds may be represented by the following graphic formulae:

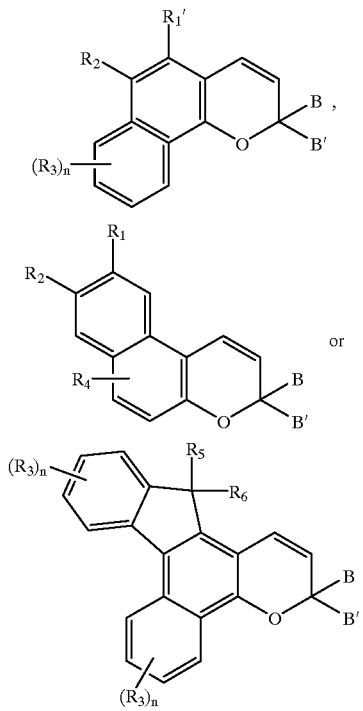

Also described are various substrates that contain or that are coated with such compounds. Optically clear articles such as contact lenses or other plastic transparencies that incorporate the novel naphthopyran compounds or combinations thereof with complementary photochromic compounds, are also described.

20 Claims, No Drawings

U.S. PATENT DOCUMENTS

| | | | |
|---|---|---|---|
| 5,252,742 A | 10/1993 | Miyashita | 548/121 |
| 5,274,132 A | 12/1993 | Van Gemert | 25/586 |
| 5,359,085 A | 10/1994 | Iwamoto et al. | 548/468 |
| 5,458,814 A | 10/1995 | Kumar et al. | 252/586 |
| 5,466,398 A | 11/1995 | Van Gemert et al. | 252/586 |
| 5,488,119 A | 1/1996 | Fischer-Reimann et al. | 552/201 |
| 5,520,853 A | 5/1996 | Rickwood et al. | 252/586 |
| 5,552,901 A | 9/1996 | Kumar | 252/586 |
| 5,573,712 A | 11/1996 | Kumar et al. | 252/586 |
| 5,578,252 A | 11/1996 | Van Gemert et al. | 252/586 |
| 5,585,042 A | 12/1996 | Knowles | 252/586 |
| 5,637,262 A | 6/1997 | Van Gemert et al. | 252/586 |
| 5,645,767 A | 7/1997 | Van Gemert | 252/586 |
| 5,658,500 A | 8/1997 | Kumar et al. | 252/586 |
| 5,658,501 A | 8/1997 | Kumar et al. | 252/586 |
| 5,744,070 A | 4/1998 | Kumar | 252/586 |
| 5,753,146 A | 5/1998 | Van Gemert et al. | 252/586 |
| 5,869,658 A | 2/1999 | Lin et al. | 544/106 |
| 5,879,592 A | 3/1999 | Kumar | 252/580 |
| 5,961,892 A | 10/1999 | Van Gemert et al. | 252/586 |
| 6,113,814 A | 9/2000 | Van Gemert et al. | 252/586 |
| 6,149,841 A | 11/2000 | Kumar | 252/586 |
| 6,153,126 A | 11/2000 | Kumar | 252/586 |
| 6,194,120 B1 | 2/2001 | Chan et al. | 430/270.1 |
| 6,197,225 B1 | 3/2001 | Tanizawa et al. | 252/586 |
| 6,203,729 B1 | 3/2001 | Breyne | 252/586 |
| 6,207,084 B1 | 3/2001 | Chan et al. | 252/586 |
| 6,210,608 B1 | 4/2001 | Chan et al. | 525/586 |

POLYMERIC MATRIX COMPATIBILIZED NAPHTHOPYRANS

CROSS REFERENCE TO RELATED APPLICATIONS

This application is a continuation-in-part of application Ser. No. 09/532,978, filed Mar. 22, 2000, abandoned, which was a continuation-in-part of application Ser. No. 09/526,232, filed Mar. 15, 2000, abandoned, which was a continuation-in-part of application Ser. No. 09/437,982 filed Nov. 10, 1999, now U.S. Pat. No. 6,113,814 and which was a continuation-in-part of application Ser. No. 09/151,911 filed Sep. 11, 1998, now abandoned.

DESCRIPTION OF THE INVENTION

The present invention relates to certain novel naphthopyran compounds. More particularly, this invention relates to photochromic naphthopyrans having substituents that make the compounds more compatible for use in different matrices, e.g., hydrophilic or hydrophobic polymeric matrices. This invention also relates to compositions and articles containing such novel photochromic compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. U.S. Pat. No. 5,458,814 describes photochromic 2,2-di-substituted-5,6-substituted-2H-naphtho[1,2-b]pyran compounds primarily for use in lenses and other plastic transparencies. These compounds have an acceptable fade rate in addition to a high activated intensity and a high coloration rate. U.S. Pat. No. 5,585,042 discloses 3,3-di-substituted-8-substituted-3H-naphtho[2,1-b]pyran compounds for similar uses. These compounds exhibit an improved solar response, a higher activating wavelength than unsubstituted naphthopyrans, and an acceptable bleach or fade rate. U.S. Pat. No. 5,645,767 describes photochromic indeno[2,1-f]naphtho[1,2-b]pyrans having a high activated intensity, an acceptable fade rate and high coloration rate.

International Patent Application WO 97/05213 describes a photochromic monomer having a photochromic dye moiety bonded to an organic spacer group which terminates with a polymerizable group. It is reported that when the photochromic monomer is incorporated into a cross-linking polymerizable casting composition, the photochromic material has a reduced sensitivity to temperature.

Although 3H-naphtho[2,1-b]pyrans, 2H-naphtho[1,2-b]pyrans and indeno[2,1-f]naphtho[1,2-b]pyrans of good intensity and reasonable fade are currently available, in certain circumstances it is desirable to modify the comparability of the photochromic compound with the substrate or host material. By making the photochromic compound more compatible with the polymeric matrix, it is less likely that the combination will demonstrate cloudiness or haze and phase separation which may become evident as the formation of crystals within the matrix or a bloom on the surface resulting from the migration of the photochromic after curing, and it is more likely that the photochromic compound will be more soluble and uniformly distributed throughout the matrix. Other properties of the photochromic compounds that may or may not be effected by the substituents of the present invention include fade and/or activation rate, saturated optical density, molar absorptivity or molar extinction coefficient, activated color and leachability from the polymeric matrix. Modifications to such properties may be done to match the same properties of complementary photochromic compounds or to enable the use of such compounds in hydrophilic or hydrophobic coatings, thin films or in rigid to flexible plastic matrices, e.g., contact lenses.

In accordance with the present invention, there have been discovered novel photochromic compounds; namely, certain 2H-naphtho[1,2-b]pyrans, 3H-naphtho[2,1-b]pyrans and indeno[2,1-f]naphtho[1,2-b]pyrans, that have at least one substituent containing terminal and/or pendant groups selected from hydroxyl, carboxyl, sulfo, sulfono, (meth)acryloxy, 2-(methacryloxy)ethylcarbamyl (—OC(O)NHC$_2$H$_4$OC(O)C(CH$_3$)=CH$_2$), epoxy or a mixture thereof. The substituent having the aforementioned groups is a residue of an alkoxylated diol or an organic polyol. Appropriate selection of the substituent, e.g., chain length, the number and type of the terminal and/or pendant groups, enables modification of the aforementioned properties. For example, an increase in the number of or altering the type of substituents on the naphthopyran having terminal groups selected from hydroxyl, carboxyl, sulfo, sulfono or a mixture thereof causes an improvement in the substituted compounds compatibility with polar or hydrophilic matrices and vice versa. Use of the polymerizable groups, epoxy, (meth)acryloxy, i.e., acryloxy or methacryloxy, or 2-(methacryloxy)ethylcarbamyl with or without the aforementioned groups on the substituent enables reacting and binding the photochromic compound into the polymeric matrix to prevent extraction or leaching of the photochromics for example, when the matrix is in contact with liquids. Depending on the location of the previously mentioned substituent(s), certain other substituents may also be present on the naphtho, pyrano and indeno portions of the afore-described compounds.

DETAILED DESCRIPTION OF THE INVENTION

In accordance with the present invention, it has been discovered that certain properties, e.g., solubility and/or compatability in hydrophilic coatings, films and plastics, leachability, fade rate, activation rate, saturated optical density, fatigue rate, and molar absorption of selected photochromic 2H-naphtho[1,2-b]pyrans, 3H-naphtho[2,1-b]pyrans and indeno[2,1-f]naphtho[1,2-b]pyrans may be modified by including on such compounds at least one substituent containing terminal and/or pendant groups selected from hydroxyl, carboxyl, sulfo, sulfono, (meth)acryloxy, 2-(methacryloxy)ethylcarbamyl, epoxy or a mixture thereof. The substituent may be located on the naphtho, indeno and/or on the pyrano portion of the naphthopyran.

Other than where otherwise indicated, all numbers expressing values, such as, wavelengths, quantities of ingredients or reaction conditions used herein are to be understood as modified in all instances by the term "about" which means near to in number, quantity, degree, etc.

The disclosures of the related applications, patents and articles cited herein describing materials and/or procedures for making materials such as extended triols, polyester polyols, polycarbonate polyols, carbohydrates, macrocyclic acetals containing lipophilic substituents, propargyl alcohols, photochromic compounds, polymeric host materials, contact lenses and coating application methods are incorporated herein, in toto, by reference.

The naphthopyrans of the present invention also may have certain other substituents. Specifically, the 2H-naphthopyrans may have substituents at the 5 and 6 positions and may have additional substituents at the 7, 8, 9 and 10 positions; the 3H-naphthopyrans may have substituents at the 8 and 9 positions and may have additional substituents at the 5 and 6 positions; and the indeno-fused naphthopyrans may have certain substituents at the 5, 6, 7, 8, 9, 10, 11, 12 or 13 positions. The aforedescribed naphthopyrans may be represented by graphic formulae I, II and III in which the internal numbers 1 through 13 identify the ring atoms of the naphthopyrans and letters a through n represent the sides of the naphthopyran rings. In the definition of the substituents shown in the following graphic formulae I, II and III, like symbols have the same meaning unless stated otherwise.

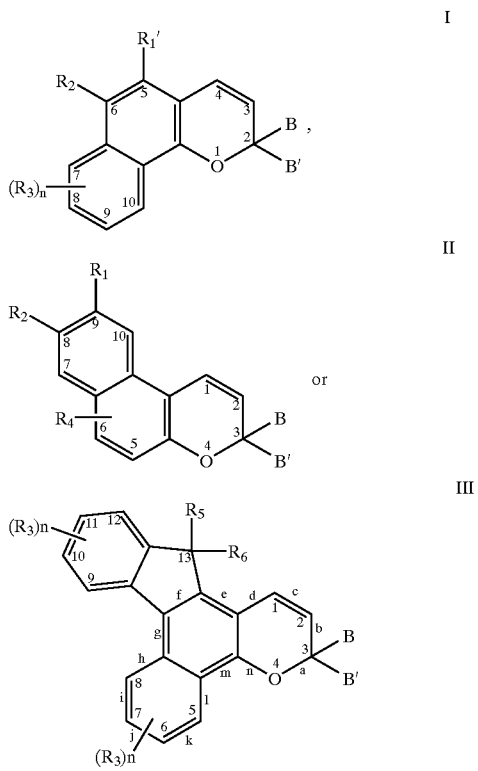

In graphic formulae I, II and III, $R_1$, $R_1'$, $R_2$, each $R_3$, $R_4$, $R_5$ and $R_6$ may be the group R. The R group may be represented by the following formulae IVA to IVF:

—A    (IVA);

—D—A    (IVB);

—D—E—U    (IVC);

—D—U    (IVD);

—E—U    (IVE);

or

—U    (IVF);

wherein —A is represented by the following formula:

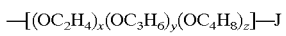

wherein —J is selected from: —OCH$_2$COOH; —OCH(CH$_3$)COOH; —OC(O)(CH$_2$)$_w$COOH; —OC$_6$H$_4$SO$_3$H; —OC$_5$H$_{10}$SO$_3$H; —OC$_4$H$_8$SO$_3$H; —OC$_3$H$_6$SO$_3$H; —OC$_2$H$_4$SO$_3$H; or —OSO$_3$H; and w is an integer from 1 to 18, preferably from 2 to 12; wherein x, y and z are each a number between 0 and 50, and the sum of x, y and z is between 1 and 50; —D— is —C(O)— or —CH$_2$—; —E— is represented by the following formula:

wherein x, y and z are the same as defined for —A; —U is a residue of an organic polyol having at least 1 hydroxyl group or a derivative of the residue wherein one or more of the hydroxyl groups have been reacted to form the carboxyl, sulfo or sulfono group containing substituent —J, a polymerizable group selected from (meth)acryloxy, 2-(methacryloxy)ethylcarbamyl, or epoxy or a mixture thereof provided that —U is not the same as —E—OH.

The group, —U, is a residue of an organic polyol which is defined herein to include hydroxylated carbohydrates discussed hereinafter. The residue is formed by the reaction of one of the hydroxyl groups on the polyol with a precursor of group —D—, such as a carboxylic acid or a methylene halide, a precursor of group —E—, such as polyalkylene glycol or a hydroxyl group as substituent $R_1$, $R_1'$, $R_2$, each $R_3$, $R_4$, $R_5$ or $R_6$ on the naphthopyran of graphic formulae I, II or III. The organic polyol may be represented by G(OH)$_a$ and the residue —U may be represented by the formula —O—G(OH)$_{a-1}$, wherein G is the backbone or main chain of the polyhydroxylated compound and a is at least 2, provided that —U is not the same as —E—OH.

All, none or at least one of the hydroxyls of group, —U, may be reacted to form a group represented by —J, a polymerizable group selected from (meth)acryloxy, 2-(methacryloxy)ethylcarbamyl, epoxy or a mixture thereof. The hydroxyl groups of —U may be reacted to form the carboxyl group containing substituent —J by the method of Reactions B and D to produce a carboxylated organic polyol residue. The organic polyol residue —U having the sulfo or sulfono terminating groups of —J on it may be produced by acidic condensation of the hydroxyl groups of —U with HOC$_6$H$_4$SO$_3$H; HOC$_5$H$_{10}$SO$_3$H; HOC$_4$H$_8$SO$_3$H; HOC$_3$H$_6$SO$_3$H; HOC$_2$H$_4$SO$_3$H; or H$_2$SO$_4$, respectively. The polymerizable groups, (meth)acryloxy, 2-(methacryloxy)ethylcarbamyl or epoxy, may be added to the polyol residue —U by condensation of the polyol with (meth)acryloyl chloride, isocyanatoethyl methacrylate or epichlorohydrin, respectively.

Examples of organic polyols that may be used as —U in the R group substituent of the polymer matrix compatibilized naphthopyrans of the present invention include polyols having at least 2 hydroxy groups such as (a) low molecular weight polyols, i.e., polyols having an average molecular weight less than 500, e.g., aliphatic triols, such as C$_2$–C$_{10}$ aliphatic triols, polyhydric alcohols and alkoxylated low molecular weight polyols; (b) polyester polyols; (c) polyether polyols; (d) amide-containing polyols; (e) epoxy polyols; (f) polyhydric polyvinyl alcohols; (g) urethane polyols; (h) polyacrylic polyols; (i) polycarbonate polyols; and (j) mixtures of such polyols.

Examples of low molecular weight polyols that can be used in the preparation of the photochromic compounds of the present invention include: tetramethylolmethane, i.e., pentaerythritol, dipentaerythritol, tripentaerythritol; trimethylolethane; trimethylolpropane; ditrimethylolpropane; 1,2,3-propanetriol, i.e., glycerol; 1,2-butanediol; di(trimethylolpropane)dimethylol propionic acid; 2-(hydroxymethyl)-2-methyl-1,3-propanediol; 2-(hydroxymethyl)-2-ethyl-1,3-propanediol; and extended polyols. Extended polyols are reaction products having terminal hydroxyl groups of the polyol and a suitable reactant, e.g., an alkylene oxide, or a lactone. Examples of such extended polyols include ε-caprolactone extended trimethylol methane and ethoxylated or propoxylated trimethylolpropane or pentaerythitol having a number average molecular weight less than 500. Extended polyols having a number average molecular weight of 500 or more are described hereinafter as polyester polyols and polyalkoxylated polyols. Further examples of extended triols are disclosed in U.S. Pat. No. 4,398,008.

Polyester polyols are generally known and can have a number average molecular weight in the range of from 500 to 10,000. They are prepared by conventional techniques utilizing low molecular weight triols and polyhydric alcohols known in the art, including but not limited to the previously described low molecular weight polyols with polycarboxylic acids. Examples of suitable polycarboxylic acids include: phthalic acid, isophthalic acid, terephthalic acid, trimellitic acid, tetrahydrophthalic acid, adipic acid, succinic acid, glutaric acid, fumaric acid, and mixtures thereof. Anhydrides of the above acids, where they exist, can also be employed and are encompassed by the term "polycarboxylic acid". In addition, certain materials that react in a manner similar to acids to form polyester polyols are also useful. Such materials include lactones, e.g., caprolactone, propiolactone and butyrolactone, and hydroxy acids such as hydroxycaproic acid and dimethylol propionic acid. If a triol or polyhydric alcohol is used, a monocarboxylic acid, such as acetic acid and/or benzoic acid, may be used in the preparation of the polyester polyols, and for some purposes, such a polyester polyol may be desirable. Moreover, polyester polyols are understood herein to include polyester polyols modified with fatty acids or glyceride oils of fatty acids and/or alkylene oxides, e.g., ethylene oxide, propylene oxide, etc., to produce polyoxyethylene fatty acid esters such as polyoxyethylene (20) sorbitan monolaurate and related polysorbates. Further examples of polyester polyols having ether and ester groups are described in U.S. Pat. No. 4,677,181.

Polyether polyols are generally known and can have a number average molecular weight in the range of from 500 to 10,000. Examples of polyether polyols include various polyoxyalkylene polyols and polyalkoxylated polyols each having at least 2 hydroxyl groups and a number average molecular weight greater than 500. The polyether polyols can be prepared, according to well-known methods, by condensing alkylene oxide, or a mixture of alkylene oxides using acid or base catalyzed addition, with a polyhydric initiator or a mixture of polyhydric initiators such as low molecular weight polyols, sorbitol and the like. Illustrative alkylene oxides include ethylene oxide, propylene oxide, butylene oxide, amylene oxide, aralkylene oxides, e.g., styrene oxide, and the halogenated alkylene oxides such as trichlorobutylene oxide and so forth. The more preferred alkylene oxides include propylene oxide and ethylene oxide or a mixture thereof using random or step-wise oxyalkylation.

Amide-containing polyols are generally known and typically are prepared from the reaction of diacids or lactones and low molecular weight polyols described herein with diamines or aminoalcohols as described hereinafter. For example, amide-containing polyols may be prepared by the reaction of neopentyl glycol, adipic acid and hexamethylenediamine. The amide-containing polyols may also be prepared through aminolysis by the reaction, for example, of carboxylates, carboxylic acids, or lactones with amino alcohols. Examples of suitable diamines and amino alcohols include hexamethylenediamines, ethylenediamines, phenylenediamine, monoethanolamine, diethanolamine, isophorone diamine and the like.

Epoxy polyols are generally known and can be prepared, for example, by the reaction of glycidyl ethers of polyphenols such as the diglycidyl ether of 2,2-bis(4-hydroxyphenyl)propane, with polyphenols such as 2,2-bis(4-hydroxyphenyl)propane. Epoxy polyols of varying molecular weights and average hydroxyl functionality can be prepared depending upon the ratio of starting materials used.

Polyhydric polyvinyl alcohols are generally known and can be prepared, for example, by the polymerization of vinyl acetate in the presence of suitable initiators followed by hydrolysis of at least a portion of the acetate moieties. In the hydrolysis process, hydroxyl groups are formed which are attached directly to the polymer backbone. In addition to homopolymers, copolymers of vinyl acetate and monomers such as vinyl chloride can be prepared and hydrolyzed in similar fashion to form polyhydric polyvinyl alcohol-polyvinyl chloride copolymers.

Urethane polyols are generally known and can be prepared, for example, by reaction of a polyisocyanate with excess organic polyol to form a hydroxyl functional product having at least 2 hydroxyl groups. Examples of polyisocyanates useful in the preparation of urethane polyols include those selected from the group consisting of aliphatic, aromatic, cycloaliphatic and heterocyclic polyisocyanates, and mixtures of such polyisocyanates.

Specific examples of polyisocyanates useful in the preparation of urethane polyols include, but are not limited to, toluene-2,4-diisocyanate; toluene-2,6-diisocyanate; diphenyl methane-4,4'-diisocyanate; diphenyl methane-2,4'-diisocyanate; para-phenylene diisocyanate; biphenyl diisocyanate; 3,3'-dimethyl-4,4'-diphenylene diisocyanate; tetramethylene-1,4-diisocyanate; hexamethylene-1,6-diisocyanate; 2,2,4-trimethyl hexane-1,6-diisocyanate; lysine methyl ester diisocyanate; bis(isocyanato ethyl) fumarate; isophorone diisocyanate; ethylene diisocyanate; dodecane-1,12-diisocyanate; cyclobutane-1,3-diisocyanate; cyclohexane-1,3-diisocyanate; cyclohexane-1,4-diisocyanate; methyl cyclohexyl diisocyanate; hexahydrotoluene-2,4-diisocyanate; hexahydrotoluene-2,6-diisocyanate; hexahydrophenylene-1,3-diisocyanate; hexahydrophenylene-1,4-diisocyanate; perhydrodiphenylmethane-2,4'-diisocyanate; perhydrodiphenylmethane-4,4'-diisocyanate and mixtures thereof.

Examples of organic polyols useful in the preparation of urethane polyols include the other polyols described herein, e.g., low molecular weight polyols, polyester polyols, polyether polyols, amide-containing polyols, epoxy polyols, polyhydric polyvinyl alcohols, polyacrylic polyols, polycarbonate polyols and mixtures thereof.

The polyacrylic polyols are generally known and can be prepared by free-radical addition polymerization techniques of monomers described hereinafter. Preferably the polyacrylic polyols have a weight average molecular weight of from 500 to 20,000 and a hydroxyl number of from 20 to 225.

Polyacrylic polyols include, but are not limited to, the known hydroxyl-functional addition polymers and copolymers of acrylic and methacrylic acids; their ester derivatives including, but not limited to, their hydroxyl-functional ester derivatives. Examples of hydroxy-functional ethylenically unsaturated monomers to be used in the preparation of the hydroxy-functional addition polymers include hydroxyethyl (meth)acrylate, i.e., hydroxyethyl acrylate and hydroxyethyl methacrylate, hydroxypropyl(meth)acrylate, hydroxybutyl (meth)acrylate, hydroxymethylethyl acrylate, hydroxymethylpropyl acrylate and mixtures thereof.

More preferably, the polyacrylic polyol is a copolymer of hydroxy-functional ethylenically unsaturated (meth)acrylic monomers and other ethylenically unsaturated monomers selected from the group consisting of vinyl aromatic monomers, e.g., styrene, α-methyl styrene, t-butyl styrene and vinyl toluene; vinyl aliphatic monomers such as ethylene, propylene and 1,3-butadiene; (meth)acrylamide; (meth)acrylonitrile; vinyl and vinylidene halides, e.g., vinyl chloride and vinylidene chloride; vinyl esters, e.g., vinyl acetate; alkyl esters of acrylic and methacrylic acids, i.e. alkyl esters of (meth)acrylic acids, having from 1 to 17 carbon atoms in the alkyl group, including methyl(meth)acrylate, ethyl(meth)acrylate, butyl(meth)acrylate, cyclohexyl(meth)acrylate, 2-ethylhexyl(meth)acrylate, isobornyl(meth)acrylate and lauryl(meth)acrylate; epoxy-functional ethylenically unsaturated monomers such as glycidyl(meth)acrylate; carboxy-functional ethylenically unsaturated monomers such as acrylic and methacrylic acids and mixtures of such ethylenically unsaturated monomers.

The hydroxy-functional ethylenically unsaturated (meth)acrylic monomer(s) may comprise up to 95 weight percent of the polyacrylic polyol copolymer. Preferably it composes up to 70 weight percent, and more preferably, the hydroxy-functional ethylenically unsaturated (meth)acrylic monomer (s) comprises up to 45 weight percent of the total copolymer.

The polyacrylic polyols described herein can be prepared by free radical initiated addition polymerization of the monomer(s), and by organic solution polymerization techniques. The monomers are typically dissolved in an organic solvent or mixture of solvents including ketones such as methyl ethyl ketones, esters such as butyl acetate, the acetate of propylene glycol, and hexyl acetate, alcohols such as ethanol and butanol, ethers such as propylene glycol mono-propyl ether and ethyl-3-ethoxypropionate, and aromatic solvents such as xylene and SOLVESSO 100, a mixture of high boiling hydrocarbon solvents available from Exxon Chemical Co. The solvent is first heated to reflux, usually 70 to 160° C., and the monomer or a mixture of monomers and free radical initiator is slowly added to the refluxing solvent, over a period of about 1 to 7 hours. Adding the monomers too quickly may cause poor conversion or a high and rapid exothermic reaction, which is a safety hazard. Suitable free radical initiators include t-amyl peroxyacetate, di-t-amyl peroxyacetate and 2,2'-azobis(2-methylbutanenitrile). The free radical initiator is typically present in the reaction mixture at from 1 to 10 percent, based on total weight of the monomers. The polymer prepared by the procedures described herein is non-gelled and preferably has a weight average molecular weight of from 500 to 20,000 grams per mole.

Polycarbonate polyols that can be used to prepare the photochromic compounds of the present invention may be obtained by reacting polyhydric alcohols with a carbonyl component selected from phosgene, a chloroformate, a dialyl carbonate, a diaryl carbonate, an alkylene carbonate or a mixture thereof. Such polycarbonate polyol production methods are described in U.S. Pat. Nos. 3,689,609, 3,689,462, 4,131,731; 4,160,853; 4,533,729, 4,891,421 and 5,266,551.

Polycarbonate polyols having 2 or more hydroxyl groups may also be prepared by the ester interchange reaction of a polycarbonate diol with a triol and/or a tetraol, as described in U.S. Pat. No. 5,143,997. Introduction of carboxyl groups into the polycarbonate polyols may be accomplished by the reaction of a polycarbonate polyol with an acid anhydride or a dicarboxylic acid, as described in U.S. Pat. No. 5,527,879.

Examples of polyhydroxylated carbohydrates that can be used in the R group substituent of the photochromic compounds of the present invention include: low molecular weight carbohydrates of the formula $C_n(H_2O)_n$ wherein n is from 3 to 5, e.g., aldotriose, aldoketose, erythrose, ribose, etc.; monosaccharides, e.g., simple sugars such as glucose and fructose; oligosaccharides, i.e., carbohydrates containing from two to ten monosaccharides linked together, e.g., sucrose and cyclodextrins; polysaccharides, i.e., carbohydrates containing more than ten monosaccharides linked together by glycosidic bonds, e.g., starch, cellulose, glycogen, pectin, agar, carrageenan and natural gums such as arabic and tragacanth.

The polyhydroxylated carbohydrates described herein also include glycosides which are mono- and oligosaccharides linked to nonsugar organic compounds. An example of which is the product of the reaction of D-glucose with ethanol to form ethyl α- & β-D-glucopyranosides. Another class of polyhydroxylated carbohydrates are the glycoconjugates composed of glycoproteins, proteoglycans, peptidoglycans and glycolipids. Still another class of carbohydrates includes various reaction products such as the sugar alcohols, e.g., xylitol and glucitol, produced by the reduction of mono- and oligosaccharides. A further group of reaction products include low molecular weight carbohydrates, mono- and oligosaccharides in which one or more of the hydroxyl groups has been oxidized to a carboxylic acid functional group, or replaced by an amino group, thiol group or a halogen atom. Further information about carbohydrates that may be suitable for use in the R-group is found in the *Kirk-Othmer Encyclopedia of Chemical Technology,* Fourth Edition, 1992, Volume 4, pages 911–948.

Preferably, the —U group is selected from low molecular weight polyols and extended polyols. Examples of such polyols include (a) glycerol, pentaerythritol and trimethylolpropane, (b) ethoxylated glycerol, ethoxylated pentaerythritol and ethoxylated trimethyolpropane; and (c) polyols (a) and (b) having at least 1 hydroxyl group reacted to produce substituent —J, a polymerizable group selected from (meth)acryloxy, 2-(methacryloxy)ethylcarbamyl or epoxy, or a mixture thereof.

The group, $—(OC_2H_4)_x—$, represents poly(ethylene oxide); $—(OC_3H_6)_y—$, represents poly(propylene oxide); and, $—(OC_4H_8)_z—$, represents poly(butylene oxide). When used in combination, the poly(ethylene oxide), poly (propylene oxide) and poly(butylene oxide) groups of R may be in a random or block order within the R moiety. The letters x, y and z are each a number between 0 and 50 and the sum of x, y and z is between 1 and 50. The sum of x, y and z may be any number that falls within the range of 1 to 50, e.g., 1, 2, 3 . . . 50. The sum may also range from any lower number to any higher number within the range of 1 to 50, e.g., 6 to 50, 31 to 50. The numbers for x, y, and z are average values and can be partial numbers, e.g., 9.5.

Alternatively, $R_1$ is hydrogen, $C_1–C_3$ alkyl or the group, —C(O)W, W being —OR$_7$, —N(R$_8$)R$_9$, piperidino or morpholino, wherein $R_7$ is allyl, $C_1–C_6$ alkyl, phenyl, mono ($C_1–C_6$)alkyl substituted phenyl, mono($C_1–C_6$)alkoxy substituted phenyl, phenyl($C_1–C_3$)alkyl, mono($C_1–C_6$)alkyl substituted phenyl($C_1–C_3$)alkyl, mono($C_1–C_6$)alkoxy substituted phenyl($C_1–C_3$)alkyl, $C_1–C_6$ alkoxy($C_2–C_4$)alkyl or $C_1–C_6$ haloalkyl; $R_8$ and $R_9$ are each selected from the group consisting of $C_1–C_6$ alkyl, $C_5–C_7$ cycloalkyl, phenyl and mono- or di-substituted phenyl, said phenyl substituents being selected from $C_1–C_6$ alkyl and $C_1–C_6$ alkoxy, and said halo substituent being chloro or fluoro. $R_1'$ is the same as $R_1$ except that $R_1'$ is not hydrogen.

$R_2$ may be selected from the group consisting of the group R, mono-R-substituted phenyl, hydrogen, $C_1–C_6$ alkyl, $C_3–C_7$ cycloalkyl, phenyl, mono- or di-substituted phenyl and the groups —OR$_{10}$ and —OC(O)R$_{10}$, wherein $R_{10}$ is $C_1–C_6$ alkyl, phenyl($C_1–C_3$)alkyl, mono($C_1–C_6$)alkyl substituted phenyl($C_1–C_3$)alkyl, mono($C_1–C_6$)alkoxy substituted phenyl($C_1–C_3$)alkyl, $C_1–C_6$ alkoxy($C_2–C_4$)alkyl, $C_3–C_7$ cycloalkyl or mono($C_1–C_4$)alkyl substituted $C_3–C_7$ cycloalkyl, n is selected from the integers 0, 1 and 2 and said phenyl substituents are the same as for $R_1$.

Each $R_3$ and $R_4$ may be selected from the group consisting of the group R, hydrogen, $C_1–C_6$ alkyl, $C_3–C_7$ cycloalkyl, phenyl, mono- or di-substituted phenyl and the groups —OR$_{10}$ and —OC(O)R$_{10}$, wherein $R_{10}$ is $C_1–C_6$ alkyl, phenyl($C_1–C_3$)alkyl, mono($C_1–C_6$)alkyl substituted phenyl ($C_1–C_3$)alkyl, mono($C_1–C_6$)alkoxy substituted phenyl ($C_1–C_3$)alkyl, $C_1–C_6$ alkoxy($C_2–C_4$)alkyl, $C_3–C_7$ cycloalkyl or mono($C_1$–$C_4$)alkyl substituted $C_3$–$C_7$ cycloalkyl, n is selected from the integers 0, 1 and 2 and said phenyl substituents are the same as for $R_1$.

$R_5$ and $R_6$ may together form an oxo group, a spiro-carbocyclic ring containing 3 to 6 carbon atoms or a spiro-heterocyclic group containing 1 or 2 oxygen atoms and 3 to 6 carbon atoms including the spirocarbon atom and both rings may be benz-annelated with one or two benzene groups. Examples of the spiro-carbocyclic ring substituents include spirofluoreno, spirocyclopropyl, spirocyclobutyl, spirocyclopentyl, spirocyclohexyl, spiroindan-1-yl, spiroindan-2-yl, etc. Examples of the spiro-heterocyclic group include spiroxantheno and compounds which may be represented by the expression (—O—($C_2$–$C_5$ alkanediyl)-O—), e.g., spiro-1,3-dioxolane-2, spiro-1,3-dioxane-2, etc., or spirolactones, such as butyrolactone, propiolactone, etc. Alternatively, $R_5$ and $R_6$ may each be the group R, hydrogen, hydroxy, $C_1$–$C_6$ alkyl, $C_3$–$C_7$ cycloalkyl, allyl, phenyl, mono-substituted phenyl, benzyl, mono-substituted benzyl, chloro, fluoro, the group —C(O)X, wherein X is hydroxy, $C_1$–$C_6$ alkyl, $C_1$–$C_6$ alkoxy, phenyl, mono-substituted phenyl, amino, mono($C_1$–$C_6$)alkylamino, or di($C_1$–$C_6$)alkylamino, e.g., dimethyl amino, methyl propyl amino, etc., or $R_5$ and $R_6$ may each be the group, —$OR_{11}$, wherein $R_{11}$ is $C_1$–$C_6$ alkyl, phenyl($C_1$–$C_3$)alkyl, mono ($C_1$–$C_6$) alkyl substituted phenyl($C_1$–$C_3$)alkyl, mono ($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, the group, —CH($R_{12}$)Y, wherein $R_{12}$ is hydrogen or $C_1$–$C_3$ alkyl and Y is CN, $CF_3$, or $COOR_{13}$, and $R_{13}$ is hydrogen or $C_1$–$C_3$ alkyl, or $R_{11}$ is the group, —C(O)Z, wherein Z is hydrogen, $C_1$–$C_6$ alkyl, $C_1$–$C_6$ alkoxy, the unsubstituted, mono- or di-substituted aryl groups, phenyl or naphthyl, phenoxy, mono- or di-($C_1$–$C_6$) alkyl substituted phenoxy, mono- or di-($C_1$–$C_6$)alkoxy substituted phenoxy, mono- or di-($C_1$–$C_6$)alkoxy substituted phenoxy, amino, mono($C_1$–$C_6$)alkylamino, di($C_1$–$C_6$) alkylamino, phenylamino, mono- or di($C_1$–$C_6$)alkyl substituted phenylamino, or mono- or di-($C_1$–$C_6$)alkoxy substituted phenylamino, each of the aforedescribed phenyl, benzyl and aryl group substituents being $C_1$–$C_6$ alkyl or $C_1$–$C_6$ alkoxy.

B and B' are each selected from the group consisting of: (a) mono-R-substituted phenyl; (b) the unsubstituted, mono-, di- and tri-substituted aryl groups, phenyl and naphthyl; (c) 9-julolidinyl and the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in (b) and (c) being selected from the group consisting of hydroxy, aryl, mono($C_1$–$C_6$)alkoxyaryl, di($C_1$–$C_6$) alkoxyaryl, mono($C_1$–$C_6$)alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl ($C_1$–$C_6$)alkyl, aryl($C_1$–$C_6$)alkoxy, aryloxy, aryloxy($C_1$–$C_6$) alkyl, aryloxy($C_1$–$C_6$)alkoxy, mono- and di-($C_1$–$C_6$) alkylaryl($C_1$–$C_6$)alkyl, mono- and di-($C_1$–$C_6$)alkoxyaryl ($C_1$–$C_6$)alkyl, mono- and di-($C_1$–$C_6$)alkylaryl($C_1$–$C_6$) alkoxy, mono- and di-($C_1$–$C_6$)alkoxyaryl($C_1$–$C_6$)alkoxy, amino, mono($C_1$–$C_6$)alkylamino, di($C_1$–$C_6$)alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ chloroalkyl, $C_1$–$C_6$ fluoroalkyl, $C_1$–$C_6$ alkoxy, mono ($C_1$–$C_6$)alkoxy($C_1$–$C_4$)alkyl, acryloxy, methacryloxy, bromo, chloro and fluoro, each aryl group described for said aryl or heteroaromatic substituent being phenyl or naphthyl; (d) the unsubstituted or mono-substituted groups, pyrazolyl, imidazolyl, pyridyl, pyrazolinyl, imidazolinyl, pyrrolinyl, phenothiazinyl, phenoxazinyl, phenazinyl or acridinyl, each of said substituents for said groups in (d) being selected from the group consisting of $C_1$–$C_6$ alkyl, $C_1$–$C_6$ alkoxy, phenyl, fluoro, chloro and bromo; (e) monosubstituted phenyl, having a substituent at the para position that is the linking group, —($CH_2$)$_t$— or —O—($CH_2$)$_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho[1,2-b]pyran; (f) the groups represented by the following graphic formulae VA and VB:

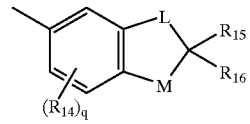

VA

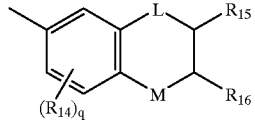

VB wherein L is carbon or oxygen and M is oxygen or substituted nitrogen, provided that when M is substituted nitrogen, L is carbon, said nitrogen substituents being selected from the group consisting of hydrogen, $C_1$–$C_6$ alkyl and $C_2$–$C_6$ acyl; each $R_{14}$ is $C_1$–$C_6$ alkyl, $C_1$–$C_6$ alkoxy, hydroxy, chloro or fluoro; $R_{15}$ and $R_{16}$ are each hydrogen or $C_1$–$C_6$ alkyl; and q is the integer 0, 1 or 2; (g) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$)-cycloalkyl, chloro($C_3$–$C_6$) cycloalkyl, fluoro($C_3$–$C_6$)cycloalkyl and $C_4$–$C_{12}$ bicycloalkyl; and (h) the group represented by the following graphic formula VC:

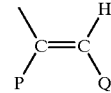

VC wherein P is hydrogen or $C_1$–$C_4$ alkyl and Q is selected from the unsubstituted, mono-, and di-substituted members of the group consisting of naphthyl, phenyl, furanyl and thienyl, each of said group substituents in (h) being $C_1$–$C_4$ alkyl, $C_1$–$C_4$ alkoxy, fluoro or chloro.

Alternatively, B and B' taken together may form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene, and cyclododecylidene, saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1] nonan-9-ylidene, bicyclo[4.3.2]undecane, and saturated $C_7$–$C_{12}$ spiro-tricyclic hydrocarbon rings, e.g., tricyclo [2.2.1.0$^{2,6}$]heptylidene, tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$–$C_4$ alkyl, $C_1$–$C_4$ alkoxy, fluoro and chloro, provided that there is at least one R group or mono-R-substituted phenyl on the naphthopyran. For example, the number of R groups (including the mono-R-substituted phenyl) may be 2, 3, 4, 5 or a number equal to the total number of substituents possible on the naphthopyran. When there is more than one R group or mono-R-substituted phenyl on the naphthopyran, the R groups may be the same or different, e.g., there may be two different groups selected from formulae IVA to IVF. Also, the naphthopyran of the present invention may have only one R-group or mono-R-substituted phenyl.

Preferably, the naphthopyran of the present invention is represented by graphic formula I or III, the R group is represented by formulae: IVA, IVB, IVE or IVF; $R_1'$ is the group R, or $R_1'$ is the group, —C(O)W, W being —$OR_7$ or —N($R_8$)$R_9$, wherein $R_7$ is $C_1$–$C_4$ alkyl, phenyl, mono ($C_2$–$C_4$)alkyl substituted phenyl, mono($C_1$–$C_4$)alkoxy substituted phenyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl($C_1$–$C_2$)alkyl, mono($C_1$–$C_4$)alkoxy($C_2$–$C_3$) alkyl or $C_1$–$C_4$ haloalkyl; $R_8$ and $R_9$ are each selected from the group consisting of $C_1$–$C_4$ alkyl, $C_5$–$C_7$ cycloalkyl, phenyl and mono- or di-substituted phenyl, said phenyl substituents being $C_1$–$C_4$ alkyl or $C_1$–$C_4$ alkoxy, and said halo substituents being chloro or fluoro. More preferably, $R_1'$ is the group R or the group, —C(O)W, wherein W is the group, —$OR_7$, and $R_7$ is a $C_1$–$C_3$ alkyl.

Preferably, $R_2$ is selected from the group consisting of the group R, mono-R-substituted phenyl, hydrogen, $C_1$–$C_3$ alkyl, $C_3$–$C_5$ cycloalkyl, phenyl, mono- or di-substituted phenyl and the group —$OR_{10}$, wherein $R_{10}$ is $C_1$–$C_4$ alkyl, phenyl($C_1$–$C_2$)alkyl, mono($C_1$–$C_4$)alkyl substituted phenyl ($C_1$–$C_2$)alkyl, mono($C_1$–$C_4$)alkoxy substituted phenyl ($C_1$–$C_2$)alkyl, $C_1$–$C_4$ alkoxy($C_2$–$C_4$)alkyl, $C_5$–$C_7$ cycloalkyl or mono($C_1$–$C_3$)alkyl substituted $C_5$–$C_7$ cycloalkyl, and the phenyl substituents are $C_1$–$C_3$ alkyl or $C_1$–$C_3$ alkoxy. More preferably, $R_2$ is selected from the group consisting of hydrogen, the group R, mono-R-substituted phenyl, $C_1$–$C_3$ alkyl, phenyl, mono- or di-substituted phenyl and the group —$OR_{10}$, wherein $R_{10}$ is $C_1$–$C_3$ alkyl and said phenyl substituents are methyl or methoxy.

Preferably, each $R_3$ is selected from the group consisting of the group R, hydrogen, $C_1$–$C_3$ alkyl, $C_3$–$C_5$ cycloalkyl, phenyl, mono- or di-substituted phenyl and the group —$OR_{10}$, wherein $R_{10}$ is $C_1$–$C_4$ alkyl, phenyl($C_1$–$C_2$)alkyl, mono($C_1$–$C_4$)alkyl substituted phenyl($C_1$–$C_2$)alkyl, mono ($C_1$–$C_4$)alkoxy substituted phenyl($C_1$–$C_2$)alkyl, $C_1$–$C_4$ alkoxy($C_2$–$C_4$)alkyl, $C_5$–$C_7$ cycloalkyl or mono($C_1$–$C_3$) alkyl substituted $C_5$–$C_7$ cycloalkyl, and the phenyl substituents are $C_1$–$C_3$ alkyl or $C_1$–$C_3$ alkoxy.

Preferably, $R_5$ and $R_6$ are each selected from the group consisting of the group R, hydrogen, hydroxy, $C_1$–$C_4$ alkyl, $C_3$–$C_6$ cycloalkyl, chloro, fluoro and the group, —$OR_{11}$, wherein $R_{11}$ is $C_1$–$C_3$ alkyl, phenyl($C_1$–$C_2$)alkyl, mono ($C_1$–$C_3$)alkyl substituted phenyl($C_1$–$C_3$)alkyl, mono ($C_1$–$C_3$)alkoxy substituted phenyl($C_1$–$C_3$)alkyl, $C_1$–$C_3$ alkoxy($C_2$–$C_4$)alkyl, $C_1$–$C_3$ chloroalkyl, $C_1$–$C_3$ fluoroalkyl, the group, —CH($R_{12}$)Y, wherein $R_{12}$ is hydrogen or $C_1$–$C_2$ alkyl and Y is CN or COO$R_{13}$, $R_{13}$ being hydrogen or $C_1$–$C_2$ alkyl, or $R_{11}$ is the group, —C(O)Z, wherein Z is hydrogen, $C_1$–$C_3$ alkyl, $C_1$–$C_3$ alkoxy, phenyl, naphthyl, the mono-substituted aryl groups, phenyl or naphthyl, phenoxy, mono- or di-($C_1$–$C_3$)alkyl substituted phenoxy, mono- or di- ($C_1$–$C_3$)alkoxy substituted phenoxy, mono($C_1$–$C_3$) alkylamino, phenylamino, mono- or di-($C_1$–$C_3$)alkyl substituted phenylamino, or mono- or di-($C_1$–$C_3$)alkoxy substituted phenylamino, each of said aryl group substituents being $C_1$–$C_3$ alkyl or $C_1$–$C_3$ alkoxy.

Preferably, B and B' are each selected from the group consisting of: (a) the mono R-substituted phenyl; (b) phenyl, mono-substituted and di-substituted phenyl; (c) the unsubstituted, mono- and di-substituted heteroaromatic groups furanyl, benzofuran-2-yl, thienyl, benzothien-2-yl, dibenzofuran-2-yl, and dibenzothien-2-yl, each of said phenyl and heteroaromatic substituents in (b) and (c) being selected from the group consisting of hydroxy, aryl, arlyoxy, aryl($C_1$–$C_3$)alkyl, amino, mono($C_1$–$C_3$)alkylamino, di($C_1$–$C_3$)alkylamino, N-($C_1$–$C_3$)alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono ($C_1$–$C_3$)alkoxy($C_1$–$C_3$)alkyl, chloro and fluoro; (d) the groups represented by graphic formulae VA and VB wherein L is carbon and M is oxygen, $R_{14}$ is $C_1$–$C_3$ alkyl or $C_1$–$C_3$ alkoxy; $R_{15}$ and $R_{16}$ are each hydrogen or $C_1$–$C_4$ alkyl; and q is 0 or 1; (e) $C_1$–$C_4$ alkyl; and (f) the group represented by graphic formula VC, wherein P is hydrogen or methyl and Q is phenyl or mono-substituted phenyl, said phenyl substituent being $C_1$–$C_3$ alkyl, $C_1$–$C_3$ alkoxy or fluoro; or B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

More preferably, the naphthopyran of the present invention is represented by graphic formula III, each $R_3$ is the group R represented by formula IVE or IVF of each $R_3$ is selected from the group consisting of hydrogen, $C_1$–$C_3$ alkyl, phenyl, mono- or di-substituted phenyl and the group —$OR_{10}$, wherein $R_{10}$ is $C_1$–$C_3$ alkyl and said phenyl substituents are methyl or methoxy. $R_5$ and $R_6$ are each the group R, hydrogen, hydroxy, $C_1$–$C_4$ alkyl or the group —$OR_{11}$, wherein $R_{11}$ is $C_1$–$C_3$ alkyl. B and B' are each selected from the group consisting of: (a) the mono-R-substituted phenyl; (b) phenyl, mono- and di-substituted phenyl, preferably substituted in the meta and/or para positions; (c) the unsubstituted, mono- and di-substituted heteroaromatic groups furanyl, benzofuran-2-yl, thienyl and benzothien-2-yl, each of said phenyl and heteroaromatic substituents in (b) and (c) being selected from the group consisting of hydroxy, $C_1$–$C_3$ alkyl, $C_1$–$C_3$ alkoxy, phenyl, indolino, fluoro and chloro; (d) the group represented by graphic formulae VA wherein L is carbon and M is oxygen, $R_{14}$ is $C_1$–$C_3$ alkyl or $C_1$–$C_3$ alkoxy; $R_{15}$ and $R_{16}$ are each hydrogen or $C_1$–$C_3$ alkyl; and q is 0 or 1; or B and B' taken together form fluoren-9-ylidene, adamantylidene, bornylidene, norbornylidene, or bicyclo[3.3.1]nonan-9-ylidene.

Compounds represented by graphic formulae I, II and III may be prepared by the following steps. In Reaction A, an excess of polyethylene glycol represented by general formula VI (wherein x is the same as for group —A or —E—) or another polyalkylene glycol is reacted with toluenesulfonyl chloride represented by graphic formula VII in the presence of pyridine (PY) at −5° C. to produce the hydroxy (polyethoxy)-p-toluenesulfonate represented by graphic formula VIII. See Bradshaw, J. S., et al, "Synthesis of Macrocyclic Acetals Containing Lipophilic Substituents", Tetrahedron, Vol. 43, No. 19, pp 4271 to 4276, 1987.

REACTION A

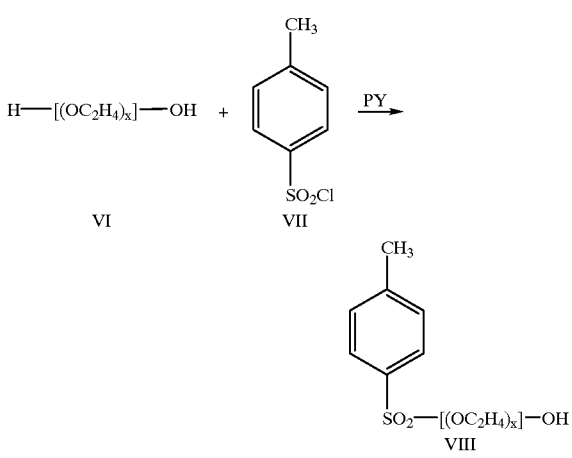

In Reaction B, the alkoxylated toluenesulfonate represented by graphic formula VIII is reacted with a naphthopyran represented by graphic formula IX in the presence of anhydrous potassium carbonate, acetone solvent and heat to form the hydroxy end-capped alkoxylated naphthopyran of graphic formula IXA. The hydroxy end-capped alkoxylated naphthopyran of graphic formula IXA is further reacted with bromoacetic acid in the presence of a suitable base such as triethylamine to produce the pyran of graphic formula IA in which the terminal hydroxy has been end-capped with a carboxy-containing functionality. Alternatively, halogenated alkoxylated alcohols may be used in place of the alkoxylated toluenesulfonate to alkylate the hydroxy functionality using the aforementioned reaction conditions. Alkylating reactions are further described in *Organic Synthesis,* Vol. 31, pages 90–93, John Wiley & Sons, New York, N.Y.

The compound represented by graphic formula IX may be prepared by coupling a substituted naphthol with a propargyl alcohol. This procedure is described in U.S. Pat. No. 5,458,814, column 5, line 10 to column 7, line 38. The propargyl alcohol may be prepared according to the methods disclosed in U.S. Pat. No. 5,645,767, column 5, line 8 to column 6, line 30.

A propargyl alcohol containing a 9-julolidinyl or other benzo-fused cyclic amino groups, e.g., indolyl and tetrahydroquinolinyl, may be prepared by the Friedel-Craft's acylation of the material with benzoyl chloride using aluminum chloride as the catalyst. The resulting amino substituted benzophenone may be reacted with sodium acetylide in a solvent such as dimethylformamide to produce a propargyl alcohol containing a benzo-fused cyclic amino substituent. The propargyl alcohol may be used in the hereinafter described coupling reaction to produce a naphthopyran having such a B or B' substituent.

REACTION B

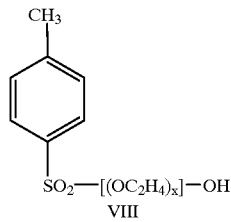

+

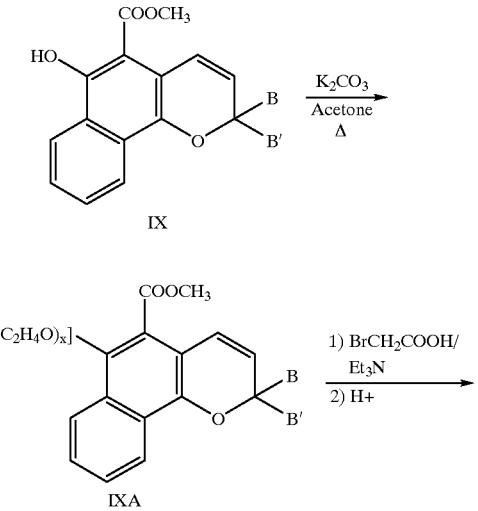

In Reaction C, a substituted naphthoic acid represented by graphic formula X is reacted with a polyethylene glycol represented by general formula VI using concentrated sulfuric acid and heat to form the alkoxylated naphthol represented by graphic formula XIA,. Alternatively X is reacted under similar conditions with glycerol to produce XIB. In graphic formula X, $R_2$ and $R_3$ are as previously defined. The alkoxylated naphthols represented by graphic formula XIA and XIB are coupled with the propargyl alcohol represented by graphic formula XII to form the alkoxylated naphthopyrans represented by graphic formula IB and IXB. Naphthopyran IXB is reacted with thionyl chloride to convert the terminal hydroxy to a chloride group. This chloride is further reacted with pentaerythritol to give polyhydroxylated naphthol represented by formula IC.

REACTION C

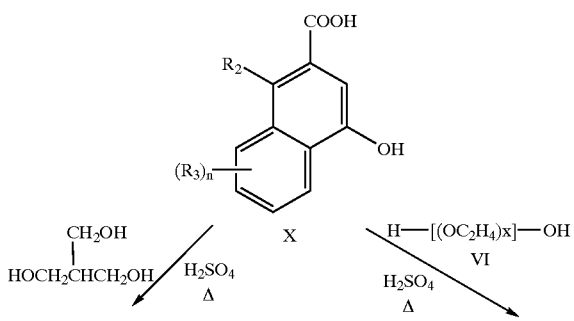

-continued

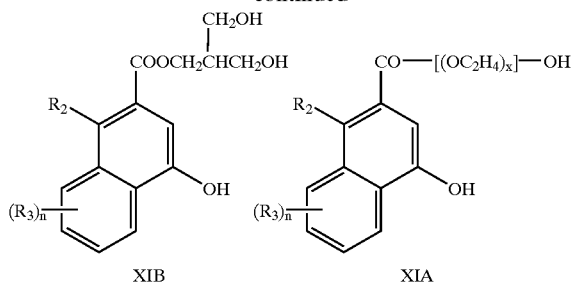

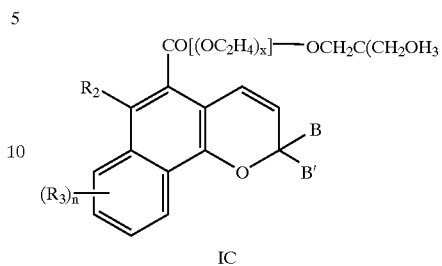

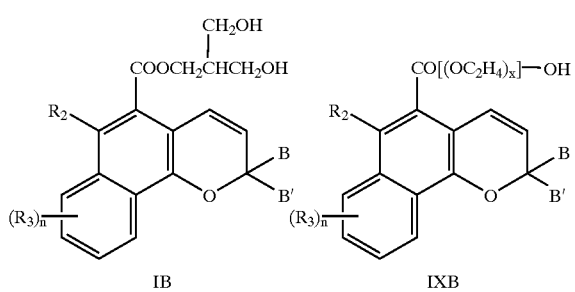

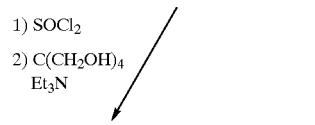

In Reaction D, the alkoxylated toluenesulfonate represented by graphic formula VIII is reacted with a hydroxy substituted benzophenone represented by graphic formula XIII to form the alkoxylated benzophenone represented by graphic formula XIV. The alkoxylated benzophenone is reacted with sodium acetylide in a suitable solvent, such as anhydrous tetrahydrofuran (THF), to form the corresponding propargyl alcohol represented by graphic formula XV. The propargyl alcohol (XV) is coupled with the substituted naphthol of graphic formula XVI to form the alkoxylated naphthopyran represented by graphic formula IXC. The terminal hydroxy group of the (poly)alkoxy grouping on naphthopyran IXC is metalated with sodium hydride, followed by reaction with succinic anhydride. Final acidification yields the carboxylated alkoxylated naphthopyran IIA.

REACTION D

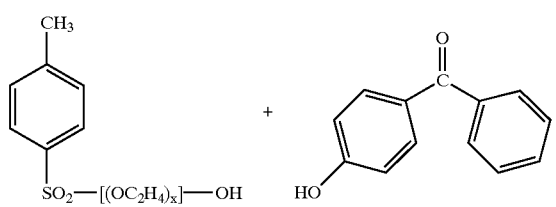

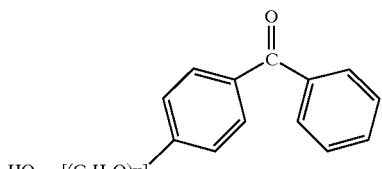

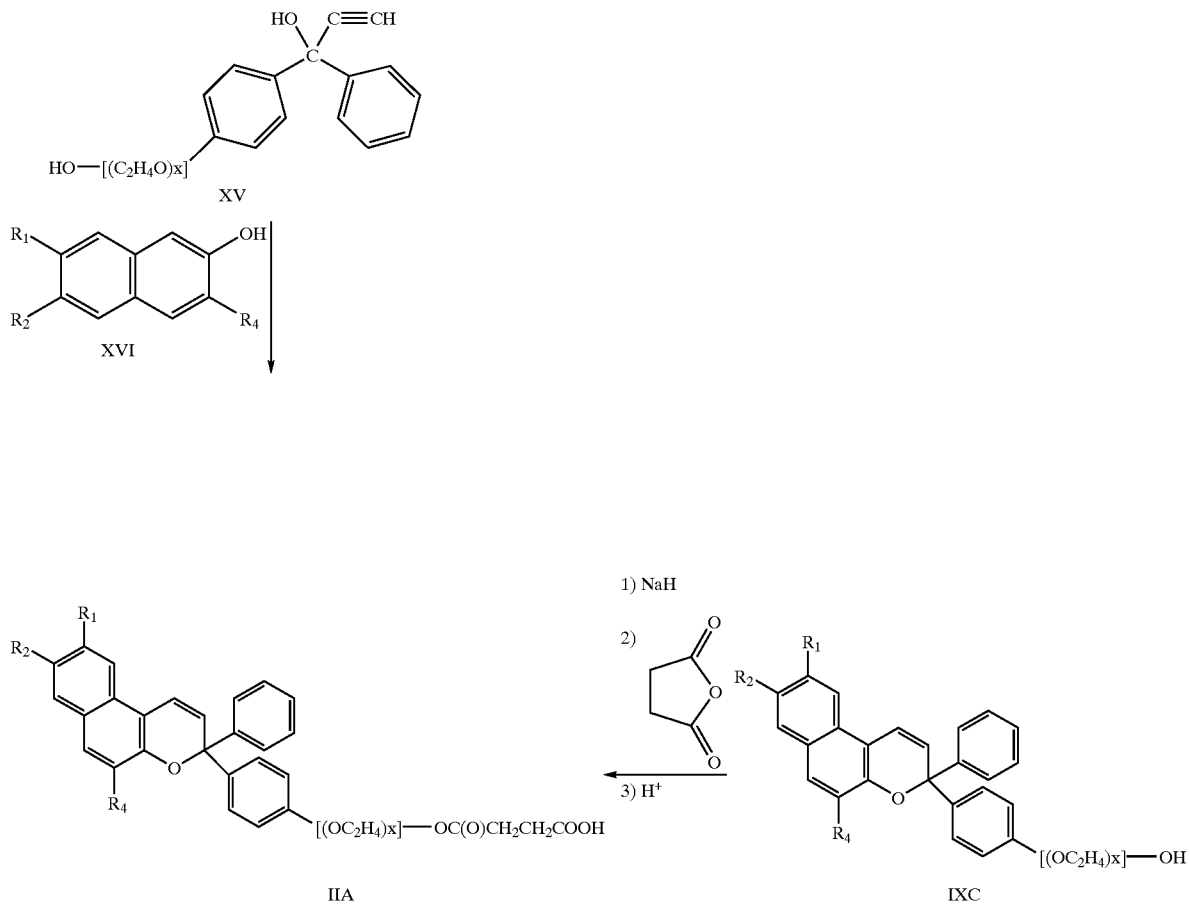

In Reaction E, glycerol is reacted with a hydroxy substituted acetophenone, benzophenone or benzaldehyde represented by graphic formula XVII in the presence of acid to form the corresponding polyhydroxylated acetophenone, benzophenone or benzaldehyde. The compound of graphic formula XVIII is reacted with an ester of succinic acid such as dimethyl succinate represented by graphic formula XIX. Addition of the reactants to a solvent, e.g., toluene, containing potassium t-butoxide or sodium hydride as the base, yields the Stobbe condensation half ester represented by graphic formula XX. The half ester (XX) undergoes cyclodehydration in the presence of acetic anhydride to form the alkoxylated acetoxynaphthalene represented by graphic formula XXI. This product is reacted with hydrochloric acid (HCl) and an anhydrous alcohol such as anhydrous methanol to form the corresponding naphthol represented by graphic formula XXII. The naphthol (XXII) is coupled with a propargyl alcohol represented by graphic formula XII to form the polyhydroxylated naphthopyran represented by graphic formula ID.

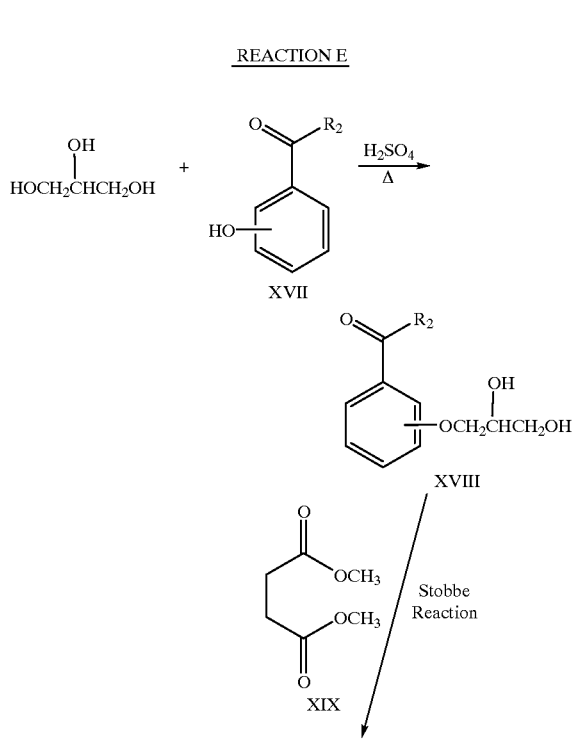

REACTION E

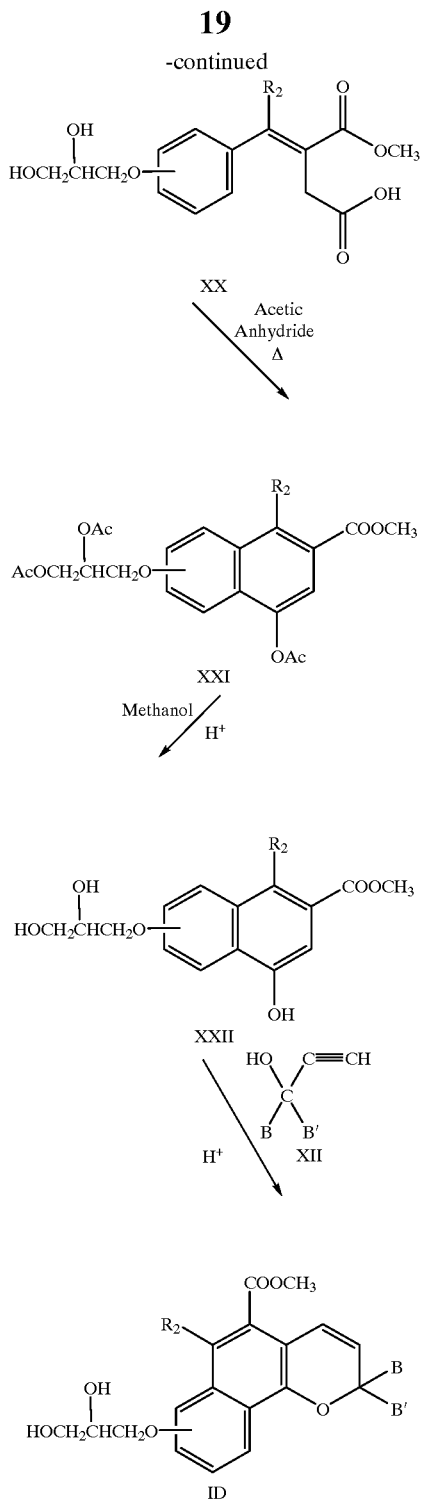

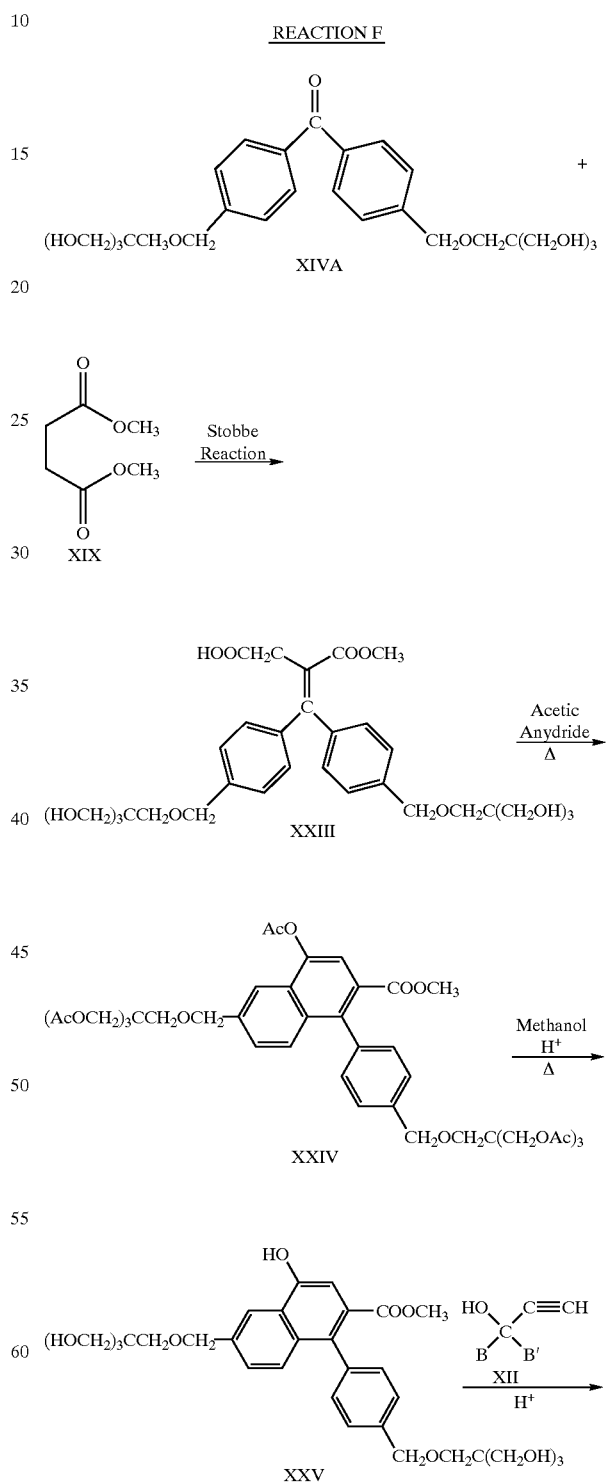

dride to form the alkoxylated acetoxynaphthalene represented by graphic formulae XXIV. This product is reacted with hydrochloric acid ($H^+$) and an anhydrous alcohol such as anhydrous methanol to form the corresponding naphthol represented by graphic formula XXV. The naphthol is coupled with propargyl alcohol represented by graphic formula XII to form the polyhydroxylated naphthopyran represented by graphic formula IE.

In Reaction F, the polyhydroxylated benzophenone represented by graphic formula XIVA (prepared by reaction of pentaerythritol with (bis)bromomethylbenzophenone in the presence of sodium hydride) is reacted with an ester of succinic acid such as dimethyl succinate represented by graphic formula XIX. Addition of the reactants to a solvent, e.g., toluene, containing potassium t-butoxide or sodium hydride as the base, yields the Stobbe condensation half esters represented by graphic formula XXIII. The half ester undergoes cyclodehydration in the presence of acetic anhy-

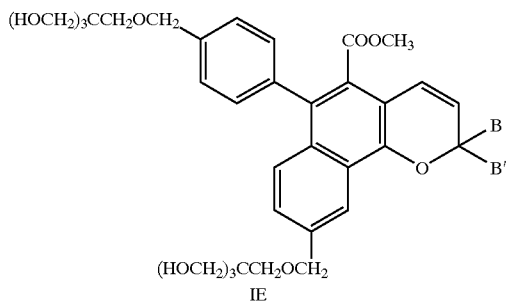

IE

In Reaction G, the compound represented by graphic formula XXIX is reduced with lithium aluminum hydride (LAH) to produce the compound represented by graphic formula XXX. Procedures for preparing the compound of graphic formula XXIX are disclosed in the afore-referenced U.S. Pat. No. 5,645,767. An ethoxylated pentaerythritol containing 4 randomly distributed ethoxy equivalents per mole is reacted with the compound of graphic formula XXX using an acid ($H^+$) to form several ethoxylated isomers including the polyhydroxylated indeno-fused naphthopyran of graphic formula IIIA.

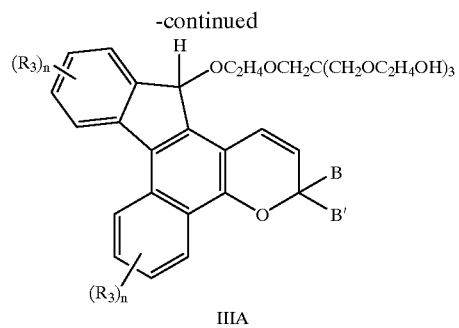

IIIA

In reactions H and I, the indeno-fused naphthopyrans represented by graphic formula XXIX may be substituted with group R as the $R_3$ substituent. For example, compound XXVII in Reaction F may be cyclized under acidic conditions and coupled with a propargyl alcohol to produce indeno-fused naphthopyrans having the R group at the 6 position. The same may be done to compound XXVIII to produce an indeno-fused naphthopyran having the R group at the 11 position.

In Reaction H, the indeno-fused naphthopyran represented by graphic formula XXIX is first reacted with compound XXXI and then cyclized under acidic conditions ($H^+$) to produce the compound represented by graphic formula IIIB. Substituents $R_{15}$ and $R_{16}$ are the same as previously described. Compound XXXI may be prepared from the corresponding phenethyl bromide via reaction with magnesium in ethereal solvents.

REACTION G

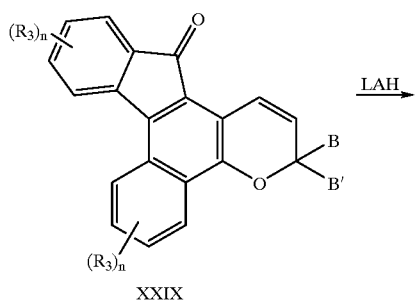

XXIX

REACTION H

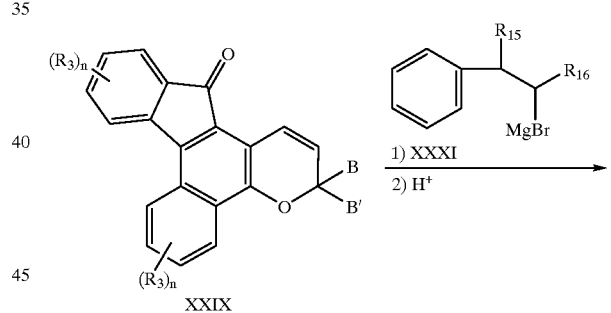

XXIX

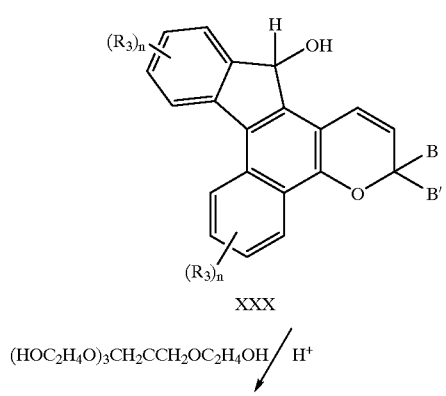

XXX

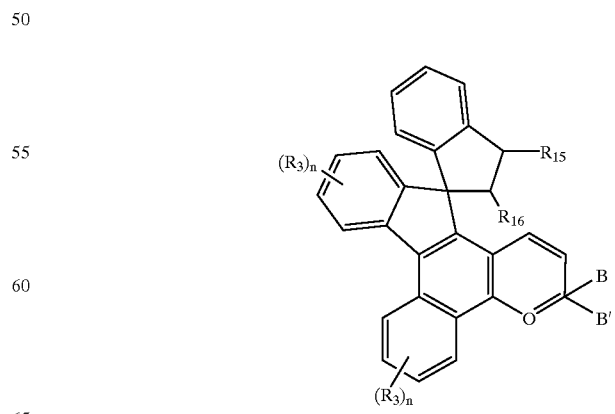

IIIB

In Reaction I, the indeno-fused naphthopyran represented by graphic formula XXIX is first reacted with compound XXXII and then cyclized under acidic conditions (H⁺) to produce the compound represented by graphic formula IIIC. T in compound XXXII may be selected from the groups, (—O—), (—CH₂—), and (—CH=CH—) and m is an integer of from 0 to 2. When T is (—CH₂—), m equals 1–2, when T is (—CH=CH—), m equals 1 and when m equals 0, T is a carbon-carbon bond.

REACTION I

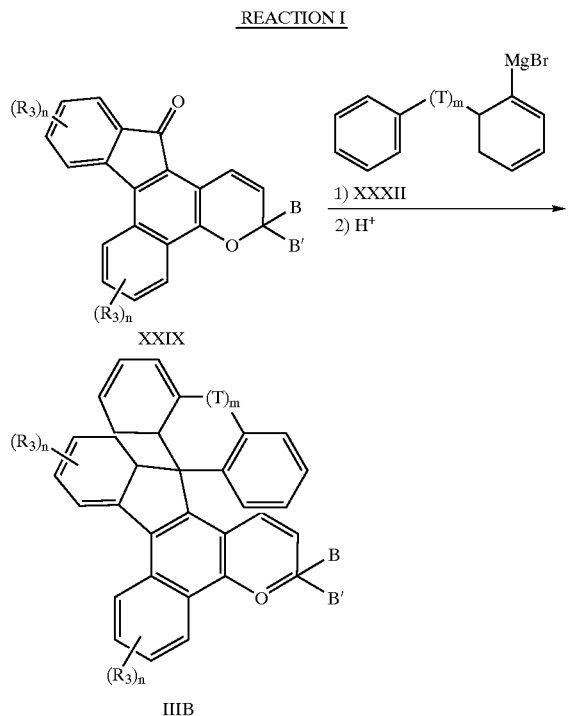

Reactions C, E, F, G, H and I produce naphthopyrans having a hydroxylated R group which may be used in reactions to form polyurethane polymers. The hydroxyl functional R group substituted naphthopyrans may also be reacted with methacryloyl chloride or methacrylic anhydride in the presence of an acid acceptor to produce a methacryloxy capped R group substituted naphthopyran or with epichlorohydrin in the presence of a base to produce an epoxy capped R group substituted naphthopyran. The hydroxylated R group may also be condensed with the appropriate sulfo- or sulfono-containing groups in the presence of acid to produce sulfo- or sulfono-capped R group substituted naphthopyrans.

The naphthopyran compounds represented by graphic formulae I, II and III may be used in those applications in which organic photochromic substances may be employed, such as optical lenses, e.g., vision correcting ophthalmic lenses, contact lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions. As used herein, coating compositions are defined herein to include polymeric coating compositions prepared from materials such as polyurethanes, epoxy resins, aminoplast resins, poly(meth)acrylate resins, polyanhydride resins and other resins used to produce synthetic polymers; paints, i.e., a pigmented liquid or paste used for the decoration, protection and/or the identification of a substrate; and inks, i.e., a pigmented liquid or paste used for writing and printing on substrates, which include paper, glass, ceramics, wood, masonry, textiles, metals and polymeric organic materials. Coating compositions may be used to produce polymeric coatings on optical elements, verification marks on security documents, e.g., documents such as banknotes, passport and drivers' licenses, for which authentication or verification of authenticity may be desired.

Depending on the R group and number of such groups used as substituents, the photochromic compounds of the present invention may be soluble in water, water soluble polymers or water containing polymers. Soluble is defined as miscible to the extent of at least 1 gram per liter. The water solubility of some of the photochromic compounds of the present invention offers handling and processing advantages not achieved by water insoluble photochromic compounds. In particular, the use of hazardous organic solvents as carriers for photochromic compounds is avoided. Also avoided is the use of such solvents in cleaning excess photochromic material from the surface of polymeric substrates after an imbibition or transfer process.

The 2H-naphtho[1,2-b]pyrans represented by graphic formula I exhibit color changes from colorless to colors ranging from yellow to red/purple. The 3H-naphtho[2,1-b]pyrans represented by graphic formula II exhibit color changes from colorless to colors ranging from yellow to orange and red. The indeno[2,1-f]naphtho[1,2-b]pyrans represented by graphic formulae III exhibit color changes from colorless to colors ranging from orange to blue/gray.

Examples of contemplated naphthopyrans within the scope of the invention are the following:

(a) 3,3-di(4-methoxyphenyl)-6,11,13-trimethyl-13-(2,3-dihydroxy)propoxy-indeno[2,1-f]naphtho[1,2-b]pyran;

(b) 3,3-di(4-methoxyphenyl)-6,11,13-trimethyl-13-(2-(2,2-bis[(2-hydroxyethoxy)methyl]-3-hydroxypropyloxy)ethoxy)-indeno[2,1-f]naphtho[1,2-b]pyran;

(c) 3,3-di(4-methoxyphenyl)-6,11-dimethoxy-13-methyl-13-(2,3-dihydroxy)propoxy-indeno[2,1-f]naphtho[1,2-b]pyran;

(d) 3-phenyl-3-(4-morpholinophenyl)-13-methyl-13-(2,3-dihydroxy)propoxy-indeno[2,1-f]naphtho[1,2-b]pyran;

(e) 2,2-diphenyl-5-((2,3-dihydroxy)propoxy)-carbonyl-8-methyl-[2H]-naphtho[1,2-b]pyran;

(f) 3,3-di(4-methoxyphenyl)-6,11,13-trimethyl-13-(2-(3-carboxypropanoyloxy)ethoxy)-indeno[2,1-f]naphtho[1,2-b]pyran;

(g) 3,3-di(4-methoxyphenyl)-6,11-dimethoxy-13-methyl-13-(2,3-dimethacryloxy)propoxyindeno[2,1-f]naphtho[1,2-b]pyran;

(h) 3,3-di(4-methoxyphenyl)-6,11,13-trimethyl-13-(2,3-di(2-sulfonoethyloxy))propoxy-indeno[2,1-f]naphtho[1,2-b]pyran;

(i) 3-phenyl-3-(4-morpholinophenyl)-6,11-dimethoxy-13-methyl-13-(2,3-di(4-sulfonophenoxy))propoxy-indeno[2,1-f]naphtho[1,2-b]pyran; and (j) 3,3-di(4-methoxyphenyl)-6,11-dimethoxy-13-methyl-13-(2,3-di(epoxymethoxy))propoxy-indeno[2,1-f]naphtha[1,2-b]pyran.

It is contemplated that the photochromic naphthopyrans of the present invention may each be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers (or substances containing the same) and which color when activated to an appropriate hue.

The complementary organic photochromic materials may include other polymerizable photochromic compounds, such as those disclosed in U.S. Pat. Nos. 4,719,296; 5,166,345; 5,236,958; 5,252,742; 5,359,085; and 5,488,119. Further examples of complementary organic photochromic compounds include other naphthopyrans and indenonaphthopyrans, chromenes and oxazines, substituted 2H-phenanthro[4,3-b]pyran and 3H-phenanthro[1,2-b]pyran compounds, benzopyran compounds having substituents at the 2-position of the pyran ring and mixtures of such photochromic compounds. Such photochromic compounds are described in U.S. Pat. Nos. 3,562,172; 3,567,605; 3,578,602; 4,215,010; 4,342,668; 4,816,584; 4,818,096; 4,826,977; 4,880,667; 4,931,219; 5,066,818; 5,238,981; 5,274,132; 5,384,077; 5,405,958; 5,429,774; 5,458,814; 5,466,398; 5,514,817; 5,552,090; 5,552,091; 5,565,147; 5,573,712; 5,578,252; 5,637,262; 5,645,767; 5,656,206; 5,658,500; 5,658,501; 5,674,432; 5,698,141; 5,723,072; 5,744,090, 5,783,116, 5,808,063, 5,811,034, 5,869,658, 5,879,592, 5,891,368 and 5,961,892. Spiro(indoline)pyrans are also described in the text, *Techniques in Chemistry,* Volume III, "Photochromism", Chapter 3, Glenn H. Brown, Editor, John Wiley and Sons, Inc., New York, 1971.

Other complementary photochromic substances contemplated are metal-dithiozonates, e.g., mercury dithizonates, which are described in, for example, U.S. Pat. No. 3,361,706; and fulgides and fulgimides, e.g., the 3-furyl and 3-thienyl fulgides and fulgimides, which are described in U.S. Pat. No. 4,931,220 at column 20, line 5 through column 21, line 38.

The photochromic articles of the present invention may contain one photochromic compound or a mixture of photochromic compounds, as desired.

The photochromic compounds of the present invention may be associated with a polymeric organic host material or other substrate by various means. They may be incorporated, i.e., dissolved and/or dispersed, into the host material, polymerized with other components of the host material, and/or incorporated into a coating applied to a substrate, e.g., a polymeric coating applied to one surface of the polymeric organic host material.

Each of the photochromic substances described herein may be used in amounts (or in a ratio) such that an organic host material or substrate to which the photochromic compounds or mixture of compounds is associated, exhibits a desired resultant color, e.g., a substantially neutral color when activated with unfiltered sunlight, i.e., as near a neutral color as possible given the colors of the activated photochromic compounds. Neutral gray and neutral brown colors are preferred. Further discussion of neutral colors and ways to describe colors may be found in U.S. Pat. No. 5,645,767 column 12, line 66 to column 13, line 19.

The amount of the photochromic naphthopyrans to be applied to or incorporated into a coating composition or host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic compounds. Typically, the more photochromic compound applied or incorporated, the greater is the color intensity up to a certain limit.

The relative amounts of the aforesaid photochromic compounds used will vary and depend in part upon the relative intensities of the color of the activated species of such compounds, the ultimate color desired and the method of application to the host material or substrate. Generally, the amount of total photochromic compound incorporated into or applied to a photochromic optical host material may range from about 0.05 to about 2.0, e.g., from 0.1 to about 1.0, milligrams per square centimeter of surface to which the photochromic compound is incorporated or applied. The amount of photochromic material incorporated into a coating composition may range from 0.1 to 40 weight percent based on the weight of the liquid coating composition.

The photochromic naphthopyrans of the present invention may be associated with the host material by various methods described in the art. See, for example, column 13, lines 40 to 58 of U.S. Pat. No. 5,645,767. Aqueous or organic solutions of the photochromic compounds may be used to incorporate the photochromic compounds into a polymeric organic host material or other materials such as textiles and polymeric coating compositions. Polymeric coating compositions may be applied to the substrate using a coating process such as that described in U.S. Pat. No. 3,971,872.

Application of the polymeric coating may be by any of the methods used in coating technology such as, for example, spray coating, spin coating, spread coating, curtain coating, dip coating, casting or roll-coating and methods used in preparing overlays, such as the method of the type described in U.S. Pat. No. 4,873,029. The application method selected also depends on the thickness of the cured coating. Coatings having a thickness ranging from 1 to 50 microns may be applied by conventional methods used in coating technology. Coatings of a thickness greater than 50 microns may require molding methods typically used for overlays.

The host material will usually be transparent, but may be translucent or even opaque. The host material need only be pervious to that portion of the electromagnetic spectrum, which activates the photochromic substance, i.e., that wavelength of ultraviolet (UV) light that produces the open or colored form of the substance and that portion of the visible spectrum that includes the absorption maximum wavelength of the substance in its UV activated form, i.e., the open form. Preferably, the host color should not be such that it masks the color of the activated form of the photochromic compounds, i.e., so the change in color is readily apparent to the observer. Compatible tints may be applied to the host material as described in U.S. Pat. No. 5,645,767 in column 13, line 59 to column 14, line 3.

Most preferably, the polymeric organic host material is a solid transparent or optically clear material, e.g., materials suitable for optical applications, such as plano, ophthalmic and contact lenses, windows, automotive transparencies, e.g., windshields, aircraft transparencies, plastic sheeting, polymeric films, etc.

Examples of polymeric organic host materials which may be used with the photochromic compounds described herein include: polymers, i.e., homopolymers and copolymers, of the bis(allyl carbonate)monomers, diethylene glycol dimethacrylate monomers, diisopropenyl benzene monomers, ethoxylated bisphenol A dimethacrylate monomers, ethylene glycol bismethacrylate monomers, poly (ethylene glycol)bismethacrylate monomers, ethoxylated phenol bismethacrylate monomers, alkoxylated polyhydric alcohol acrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, of mono-functional acrylate and/or methacrylate monomers, polyfunctional, e.g., di- or multifunctional, acrylate and/or methacrylate monomers, poly ($C_1$–$C_{12}$ alkyl methacrylates), such as poly(methyl methacrylate), poly(oxyalkylene)dimethacrylate, poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly (vinylpyrrolidone), poly((meth)acrylamide), poly (dimethylacrylamide), poly(hydroxyethyl methacrylate) poly((meth)acrylic acid), polyurethanes, polythiourethanes, thermoplastic polycarbonates, polyesters, poly(ethylene terephthalate), polystyrene, poly(alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Further examples of polymeric organic host materials are disclosed in the U.S. Pat. No. 5,753,146, column 8, line 62 to column 10, line 34.

Transparent copolymers and blends of transparent polymers are also suitable as host materials. Preferably, the host material or substrate for the photochromic polymeric coating composition is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate)monomer, especially diethylene glycol bis(allyl carbonate), which monomer is sold under the trademark CR-39, and polymerizates of copolymers of a polyol(allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polythiourethanes, polymers of members of the group consisting of diethylene glycol dimethacrylate monomers, diisopropenyl benzene monomers, ethoxylated bisphenol A dimethacrylate monomers, ethylene glycol bis-methacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly contemplated is use of the photochromic naphthopyrans of the present invention with optical organic resin monomers used to produce optically clear coatings and polymerizates, i.e., materials suitable for optical applications, such as lenses for use in a pair of spectacles, e.g., plano or ophthalmic spectacle lenses, or for use as contact lenses. Optically clear polymerizates may have a refractive index that may range from about 1.35 to about 1.75, e.g., from about 1.495 to about 1.66.

Specifically contemplated are polymerizates of optical resins sold by PPG Industries, Inc. under the CR-designation, e.g., CR-307 and CR-407, and polymerizates prepared for use as hard or soft contact lenses. Methods for producing both types of contact lenses are disclosed in U.S. Pat. No. 5,166,345, column 11, line 52, to column 12, line 52.

Additional polymerizates contemplated for use with the photochromic naphthopyrans of the present invention are polymerizates used to form soft contact lenses with high moisture content described in U.S. Pat. No. 5,965,630 and extended wear contact lenses described in U.S. Pat. No. 5,965,631.

The present invention is more particularly described in the following examples which are intended as illustrative only, since numerous modifications and variations therein will be apparent to those skilled in the art.

EXAMPLE 1

Step 1

Potassium t-butoxide (75 grams, 0.67 mole) was added to a reaction flask containing 200 milliliters (mL) of toluene. The reaction flask was equipped with an overhead stirrer, dropping funnel, and a condenser with nitrogen inlet. The contents of the reaction flask was heated to reflux temperature and a mixture of 4,4'-dimethylbenzophenone (105 grams, 0.5 mole), dimethyl succinate (90 grams, 0.62 mole), and toluene (200 grams) was added over a period of one-half hour. The resulting pasty mixture was refluxed an additional two hours, cooled, and about 400 mL of water was added and mixed well. The aqueous layer was separated, acidified with dilute hydrochloric acid, and extracted with 200 mL of toluene. The solvents, toluene and residual t-butanol, were removed on the rotary evaporator to produce a near quantitative yield of crude half-ester, 4,4-di(4-methylphenyl)-3-methoxycarbonyl-3-butenoic acids. This material was not purified further but was used directly in the next step.

Step 2

The crude half-ester from Step 1 was added to a reaction flask containing 200 mL of toluene. Acetic anhydride (100 grams) and anhydrous sodium acetate (15 grams) were added and the mixture was refluxed for 17 hours. The mixture was cooled and the solvent, toluene, was removed on a rotary evaporator. The resulting residue was dissolved in 200 mL of methylene chloride and stirred. Water (200 mL) was added followed by the slow addition of solid sodium carbonate until carbon dioxide evolution ceased. The methylene chloride layer was separated and washed with water. The solvent, methylene chloride, was removed on a rotary evaporator to yield about 100 grams of crystalline solid. The recovered product, 1-(4-methylphenyl)-2-methoxycarbonyl-4-acetoxy-6-methyl naphthalene, had a melting point of 144–146° C.

Step 3

The product from Step 2 (about 100 grams) was added to a reaction flask containing 350 mL of a 10 weight percent aqueous sodium hydroxide solution and 50 mL of methanol. The mixture was refluxed for one hour, cooled, then slowly poured into a beaker containing approximately one liter of cold (approx. 4° C.) dilute hydrochloric acid. About 100 grams of the resulting crystalline product, 1-(4-methylphenyl)-4-hydroxy-6-methyl-2-naphthoic acid, having a melting point of 210–213° C., was collected by vacuum filtration.

Step 4

The product from Step 3 (about 100 grams) was added to a reaction flask containing xylene (250 grams) and 250 grams of a 85 weight percent phosphoric acid solution. The stirred mixture was refluxed in a one liter flask equipped with a Dean-Stark trap for 20 hours. During this time a solid product formed. The mixture was cooled and 200 mL of water was added. The solid was broken up with a spatula, filtered, and washed successively with water, 5 weight percent aqueous sodium bicarbonate, and water. Ninety grams of the product, 3,9-dimethyl-5-hydroxy-7H-benzo[C]-fluoren-7-one, were recovered by vacuum filtration.

Step 5

The product from Step 4 (10 grams) was added to a reaction flask containing 1,1-di(4-methoxyphenyl)-2-propyn-1-ol (10 grams) and 100 mL of toluene. The resulting mixture was stirred and heated to 50° C., three drops of dodecylbenzene sulfonic acid were added, and the reaction mixture was kept at 50° C. for five hours. After the reaction mixture cooled to room temperature, it was filtered and the collected filtrate was washed three times with 5 weight percent aqueous sodium hydroxide. The solvent, toluene, was removed on a rotary evaporator and the desired product crystallized on the addition of acetone to the residue. The solid was vacuum filtered, washed with fresh acetone, and dried to yield 16 grams of a product having a melting point of 227–229° C. An NMR showed the product to have a structure consistent with 3,3-di(4-methoxyphenyl)-6,11-dimethyl-13-oxo-indeno[2,1-f]naphtho[1,2-b]pyran.

Step 6

The product of Step 5 (10 grams) was added to a reaction flask containing 50 mL of anhydrous tetrahydrofuran. The mixture was cooled in an ice bath and protected from moisture with a nitrogen pad while an excess of methyl Grignard reagent was added to the reaction with stirring. After stirring an additional ten minutes, 200 mL of 5 weight percent aqueous hydrochloric acid was added and the organic layer was separated and washed with water. The solvent, tetrahydrofuran, was removed on a rotary evaporator. The addition of approximately ten milliliters of a 2:1 mixture of hexane:ethyl acetate to the residue caused the crystallization of a non-photochromic material. This material was separated by filtration. The filtrate was column chromatographed on silica using a 3:1 mixture of hexane-:ethyl acetate as elutant. The desired product, which crystallized from a methanol mixture, was filtered and dried to yield 8 grams of a product having a melting point of 233–235° C. An NMR spectrum showed the product to have a structure consistent with 3,3-di(4-methoxyphenyl)-6,11, 13-trimethyl-13-hydroxy-indeno[2,1-f]naphtho[1,2-b] pyran.

Step 7

The product from Step 6 (6.0 grams) was added to a reaction flask containing 100 mL glycerol, 100 mL of tetrahydrofuran, and 2 mL of 37% hydrochloric acid. The reaction was heated to 60° C. and maintained at that temperature for 8 hours with stirring. The reaction mixture was added to 300 mL of water and 100 mL of ethyl acetate was added. The organic layer was separated, washed with water, filtered, and the solvent, ethyl acetate, was removed on a rotary evaporator. The resulting residue was chromatographed on silica using ethyl acetate (95%) and methanol (5%) as the eluant. The photochromic fractions were combined, the solvent was evaporated, and the desired product was induced to crystallize from a hexane/diethyl ether mixture. The recovered crystals were dried and filtered to yield 3 grams of product having a melting point range of 199–202☐ C. An NMR spectrum showed the product to have a structure consistent with 3,3-di(4-methoxyphenyl)-6,11,13-trimethyl-13-(2,3-dihydroxy)propoxy-indeno[2,1-f]naphtho[1,2-b]pyran.

EXAMPLE 2

The process of Example 1 was followed except that in Step 7, pentaerythritol ethoxylate (3/4 EO/OH)(available from Aldrich), 150 mL, was used instead of glycerol and 6.0 grams of 3,3-di(4-methoxyphenyl)-6,11,13-trimethyl-13-hydroxy-indeno[2,1-f]naphtho[1,2-b]pyran was used. The residue was chromatographed on silica using acetonitrile (95%) and methanol (5%) as the eluant. The recovered oil was dried to yield 2 grams of product. An NMR spectrum showed the product to have a structure consistent with 3,3-di(4-methoxyphenyl)-6,11,13-trimethyl-13-(2-(2,2-bis [(2-hydroxyethoxy)methyl]-3-hydroxypropyloxy)ethoxy)-indeno[2,1-f]naphtho[1,2-b]pyran.

EXAMPLE 3

Step 1

The process of Example 1 was followed except that in Step 7, ethylene glycol, 100 mL, was used instead of glycerol, 8.0 grams of 3,3-di(4-methoxyphenyl)-6,11,13-trimethyl-13-hydroxy-indeno[2,1-f]naphtho[1,2-b]pyran was used and as the eluant ethyl acetate (50%) and hexane (50%) was used. The photochromic fractions were combined, the solvent was evaporated, and the desired product was induced to crystallize from a hexane/diethyl ether mixture. The recovered crystals were dried and filtered to yield 5 grams of product, 3,3-di(4-methoxyphenyl)-6,11, 13-trimethyl-13-((2-hydroxy)ethyloxy)-indeno[2,1-f] naphtho[1,2-b]pyran.

Step 2

The product of Step 1, 1.8 grams, was added to a reaction flask containing 50 mL of toluene. Triethyl amine (1 ml) and succinic anhydride (0.6 grams ) were added to the mixture which was then heated to reflux for 60 minutes. The reaction mixture was washed with water and extracted with ethyl acetate. The organic layer was then concentrated. The desired product, which crystallized from a ethyl acetate/ hexane mixture, was filtered and dried to yield 1.5 grams of a product having a melting point of 175–177° C. An NMR spectrum showed the product to have a structure consistent with 3,3-di(4-methoxyphenyl)-6,11,13-trimethyl-13-(2-(3-carboxypropanoyloxy)ethyloxy)-indeno[2,1-f]naphtho[1,2-b]pyran.

EXAMPLE 4

The process of Example 1 was followed except that in Step 1, 4,4'-dimethoxybenzophenone (105 grams, 0.5 mole) was used in place of 4,4'-dimethylbenzophenone to produce 4,4-di(4-methoxylphenyl)-3-methoxycarbonyl-3-butenoic acid. This Stobbe half ester was used in Step 2 to produce 100 grams of 1-(4-methoxyphenyl)-2-methoxycarbonyl-4-acetoxy-6-methoxy naphthalene. In Step 3, 1-(4-methoxyphenyl)-2-methoxycarbonyl-4-acetoxy-6-methoxy naphthalene was used in place of 1-(4-methylphenyl)-2-methoxycarbonyl-4-acetoxy-6-methyl naphthalene to produce 1-(4-methoxyphenyl)-4-hydroxy-6-methoxy-2-naphthoic acid. In Step 4, 100 grams of this product was used in place of 1-(4-methylphenyl)-4-hydroxy-6-methyl-2-naphthoic acid and mixed with xylene (250 grams) and 250 grams of a 85 weight percent phosphoric acid solution. The stirred mixture was refluxed in a one liter flask equipped with a Dean-Stark trap for 20 hours to produce 90 grams of 3,9-dimethoxy-5-hydroxy-7H-benzo[C]-fluoren-7-one, of which 10.0 grams was used in Step 6 with 10.0 grams of 1,1-di(4-methoxyphenyl)-2-propyn-1-ol. The resulting product, 3,3-di(4-methoxyphenyl)-6,11-dimethoxy-13-oxo-indeno[2,1-f]naphtho[1,2-b]pyran, was used in Step 6, as described in Example 1, except that an ethyl acetate/hexane mixture was used to crystallize the product. Six grams of 3,3-di(4-methoxyphenyl)-6,11-dimethoxy-13-hydroxy-13-methyl-indeno[2,1-f]naphtho[1,2-b]pyran were recovered. In Step 7, six grams of the product from Step 6 and 50 ml of tetrahydrofuran were used. Three grams of the desired product, having a melting point range of 169–172☐ C., were recovered. An NMR spectrum showed the product to have a structure consistent with 3,3-di(4-methoxyphenyl)-6,11-dimethoxy-13-methyl-13-(2,3-dihydroxy)propoxy-indeno [2,1-f]naphtho[1,2-b]pyran.

EXAMPLE 5

The process of Example 1 was followed except that in Step 1, benzophenone (105 grams, 0.5 mole) was used in place of 4,4'-dimethylbenzophenone to produce 4,4-diphenyl-3-methoxy-carbonyl-3-butenoic acid. This Stobbe half ester was used in Step 2 to produce 1-phenyl-2-methoxycarbonyl-4-acetoxy-naphthalene. In Step 3, 1-phenyl-2-methoxycarbonyl-4-acetoxy-naphthalene was used in place of 1-(4-methylphenyl)-2-methoxycarbonyl-4-acetoxy-6-methyl naphthalene to produce 1-phenyl-4-hydroxy-2-naphthoic acid. In Step 4, 100 grams of the product of Step 3 and 250 grams of a 85 weight percent phosphoric acid solution were used. The stirred mixture was heated to 190–200° C. in a one liter flask for 1 hour to produce 90 grams of 5-hydroxy-7H-benzo[C]-fluoren-7-one, of which 10.0 grams was used in Step 6 with 10.0 grams of 1-phenyl-1-(4-morpholinophenyl)-2-propyn-1-ol. The resulting product, 3-phenyl-3-(4-morpholinophenyl)-13-oxo-indeno[2,1-f]naphtho[1,2-b]pyran, was used in Step 6, as described in Example 1, except that an ethyl acetate/hexane mixture was used to crystallize the product. Seven grams of 3-phenyl-3-(4-morpholinophenyl)-13-methyl-13-hydroxy-indeno[2,1-f]naphtho[1,2-b]pyran. In Step 7, six grams of the product of Step 6 and 50 ml of tetrahydrofuran were used. An NMR spectrum showed the product, 3 grams of oil, to have a structure consistent with 3-phenyl-3-(4-morpholinophenyl)-13-methyl-13-(2,3-dihydroxy)propoxy-indeno[2,1-f]naphtho[1,2-b]pyran.

EXAMPLE 6

7-Methyl-4-hydroxy-2-naphthoic acid (6 grams) and 1,1-diphenyl-2-propyn-1-ol (5 grams) were added to a reaction flask (equipped with a magnetic stirrer, Stark trap and condenser) containing 100 mL of chloroform and stirred. A catalytic amount of p-toluenesulfonic acid (about 100 milligrams) was added, and the mixture was heated to reflux and stirred for 2 hours. Afterwards, the reaction mixture was washed with water and the remaining solvent was removed under vacuum. The resulting product, 2,2-diphenyl-5-carboxylic acid-8-methyl-[2H]-naphtho[1,2-b]pyran, was induced to crystallize from a ethyl acetate/hexanes mixture to yield 4.0 grams of orange crystals.

Step 2

Four grams of 2,2-diphenyl-5-carboxylic acid-8-methyl-[2H]-naphtho[1,2-b]pyran was added to a reaction flask containing 50 mL of methylene chloride and 3.5 grams of oxalyl chloride. The mixture was stirred for sixteen hours. The methylene chloride and oxalyl chloride were removed under vacuum and the resulting mixture, containing mostly of 2,2-diphenyl-5-carboxychloride-8-methyl-[2H]-naphtho[1,2-b]pyran, was used directly in the next step.

Step 3

Thirty mL of glycerol was added to the crude material from Step 2. The mixture was heated to 60° C. and 1 ml of triethyl amine was added dropwise over 20 minutes. The reaction is held at 60° C. for 1 hour and then quenched in water and extracted twice with ethyl acetate. The organic layer is concentrated and the resulting residue was chromatographed on silica using ethyl acetate (70%) and hexane (30%) as the eluant. The photochromic fractions were combined, the solvent was evaporated, and the desired product was induced to crystallize from an ethyl acetate/hexanes mixture. The recovered yellow crystals were dried and filtered to yield 2.5 grams of product having a melting point of 180–181° C. An NMR spectrum showed the product to have a structure consistent with 2,2-diphenyl-5-((2,3-dihydroxy)-propoxy)carbonyl-8-methyl-[2H]-naphtho[1,2-b]pyran.

Comparative Example 1

The process of Example 1 was followed except that Step 7 was omitted. An NMR spectrum showed the product to have a structure consistent with 3,3-di(4-methoxyphenyl)-6,11,13-trimethyl-13-hydroxy-indeno[2,1-f]naphtho[1,2-b]pyran.

Comparative Example 2

The process of Example 4 was followed except that Step 7 was omitted. Three grams of the desired product, having a melting point of 241–242° C., were recovered. An NMR spectrum showed the product to have a structure consistent with 3,3-di(4-methoxyphenyl)-6,11-dimethoxy-13-methyl-13-hydroxy-indeno[2,1-f]naphtho[1,2-b]pyran.

Comparative Example 3

The process of Example 5 was followed except that Step 7 was omitted. Three grams of the desired product, having a melting point of 180–181° C., were recovered. An NMR spectrum showed the product to have a structure consistent with 3-phenyl-3-(4-morpholinophenyl)-13-methyl-13-hydroxy-indeno[2,1-f]naphtho[1,2-b]pyran.

Comparative Example 4

Step 1

7-Methyl-4-hydroxy-2-naphthoic acid (6 grams) and 1,1-diphenyl-2-propyn-1-ol (5 grams) were added to a reaction flask (equipped with a magnetic stirrer, Stark trap and condenser) containing 100 mL of chloroform and stirred. A catalytic amount of p-toluenesulfonic acid (about 100 milligrams) was added, and the mixture was heated to reflux and stirred for 2 hours. Afterwards, the reaction mixture was washed with water and the remaining solvent was removed under vacuum. The resulting product, 2,2-diphenyl-5-carboxylic acid-8-methyl-[2H]-naphtho[1,2-b]pyran, was induced to crystallize from a ethyl acetate/hexanes mixture to yield 4.0 grams of orange crystals.

Step 2

The product of Step 1 was added to a reaction flask containing 100 mL of methanol. One mL of 37 weight percent HCl was added and the mixture was heated to reflux for 4 hours. Upon cooling a yellow crystalline material precipitated out of solution having a melting point of 187–188□ C. This material was vacuum filtered yielding 2 grams of material having a melting point of 187–188° C. This product had an NMR spectrum consistent with 2,2-diphenyl-5-methoxycarbonyl-8-methyl-[2H]-naphtho[1,2-b]pyran.

EXAMPLE 7

Part A

Testing was done with the photochromic compounds described in the Examples and the Comparative Examples in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold it at 60° C. for 16 hours. After the mold was opened, the polymer sheet was cut using a diamond blade saw into 2 inch (5.1 centimeters) test squares.

Part B

The photochromic test squares prepared in Part A were tested for photochromic response on an optical bench. Prior to testing on the optical bench, the photochromic test squares were conditioned, i.e., exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 300 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliWatts per square centimeter (mW/cm$^2$). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density ($\Delta OD$) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\%Ta)$, where %Ta is the percent transmittance in the activated state and the logarithm is to the base 10.

The optical properties of the photochromic compounds in the test squares are reported in Table 1. When comparing results, Comparative Example 1 is the corresponding compound of, i.e., should be compared to, Examples 1, 2 and 3, CE 2 should be compared to Example 4, CE 3 should be compared to Example 4 and CE 4 should be compared to Example 6. In each comparison, the Comparative Example compound has the same structure as the Example compound except for the R group. The $\Delta$ OD/Min, which represents the sensitivity of the photochromic compound's response to UV light, was measured over the first five (5) seconds of UV exposure, then expressed on a per minute basis. The saturation optical density ($\Delta$ OD@ Saturation) was taken under identical conditions as the $\Delta$ OD/Min, except UV exposure was continued for 15 minutes. The Bleach Rate (T 1/2) is the time interval in seconds for the absorbance of the activated form of the photochromic compound in the test squares to reach one half the highest absorbance at room temperature (72° F., 22.2° C.) after removal of the source of activating light.

Part C

The lambda ($\lambda$) max (UV), which is the wavelength of the ultraviolet range closest to the visible spectrum at which the absorption of the photochromic compound occurs, for the Examples and Comparative Examples was determined using the test squares of Part A on the optical bench of Part B or by a comparable method. In the comparable method, the Example and Comparative Example compounds were dissolved in diethylene glycol dimethyl ether. The concentration of the resulting solutions was approximately 0.5 milligram per milliliter. Each solution was tested in a UV spectrophotometer to determine the $\lambda$ max (UV). The results are reported in Table 2.

The lambda max (Vis) is the wavelength in the visible spectrum at which the maximum absorption of the activated (colored) form of the photochromic compound in a test square occurs. The lambda max (Vis) wavelengths reported in Table 2 were determined by testing the photochromic test squares polymerizates of Part A on the optical bench of Part B.

The molar absorption or molar extinction coefficient ($\epsilon$) reported in Table 2 is equal to the absorbance of the photochromic compound in a diethylene glycol dimethyl ether solution at the $\lambda$ max in the UV (A) divided by the path length of the spectrophotometer cell (b) multiplied by the concentration of the photochromic compound solution in moles per liter (M) according to the formula: $\epsilon = A/bM$. The molar absorptivity was measured in a UV spectrophotometer for a $2 \times 10^{-3}$ molar solution of Example and Comparative Example compounds in a 0.1 centimeter quartz cell or by another comparable method.

TABLE 1

| Compound Example | Sensitivity $\Delta OD/min$ | $\Delta OD$ @ Saturation | Bleach Rate T 1/2 (sec) |
|---|---|---|---|
| 1 | 0.32 | 0.63 | 98 |
| 2 | 0.35 | 0.58 | 87 |
| 3 | 0.31 | 0.51 | 91 |
| CE 1 | 0.27 | 0.50 | 119 |
| 4 | 0.42 | 0.80 | 162 |
| CE 2 | 0.39 | 0.68 | 140 |
| 5 | 0.32 | 0.60 | 116 |
| CE 3 | 0.41 | 0.60 | 102 |
| 6 | 0.39 | 0.35 | 36 |
| CE 4 | 0.27 | 0.37 | 71 |

TABLE 2

| Compound Example | $\lambda$ max (nm) UV | Molar Absorpt. ($\epsilon$) | $\lambda$ max (nm) Vis (minor) | $\lambda$ max (nm) Vis (major) |
|---|---|---|---|---|
| 1 | 361 | 13283 | 442 | 569 |
| 2 | 361 | 11863 | 441 | 572 |
| 3 | 361 | 12636 | 440 | 570 |
| CE 1 | 359 | 10397 | 440 | 575 |
| 4 | 359 | 10443 | 449 | 597 |
| CE 2 | 359 | 9026 | 448 | 598 |
| 5 | 360 | 11412 | 480 | 587 |
| CE 3 | 359 | 11100 | 474 | 595 |
| 6 | 369 | 5478 | — | 467 |
| CE 4 | 368 | 4346 | — | 467 |

The results of Table 1 show that the photochromic test squares of Examples 1, 2 and 3 had somewhat higher levels of Sensitivity and $\Delta OD$@Saturation and lower Bleach Rates than Comparative Example (CE)1. Test squares containing the compound of Example 4 showed higher results than CE-2 in each test. Example 5 test squares had a lower result for Sensitivity, no change in ΔOD@Saturation and a higher Bleach Rate than CE-3. The test squares containing Example 6 had a higher result for Sensitivity, somewhat lower result for ΔOD@Saturation and nearly a 50% reduction in Bleach Rate as compared to CE-4.

The results of Table 2 reveal minor differences between the λ max UV and λ max Visible (major and minor) for the samples containing the Examples and Comparative Examples. In each case, the Examples of the present invention show a higher Molar Absorption than their respective Comparative Examples.

The present invention has been described with reference to specific details of particular embodiments thereof. It is not intended that such details be regarded as limitations upon the scope of the invention except insofar as to the extent that they are included in the accompanying claims.

We claim:

1. A naphthopyran compound represented by the following graphic formulae:

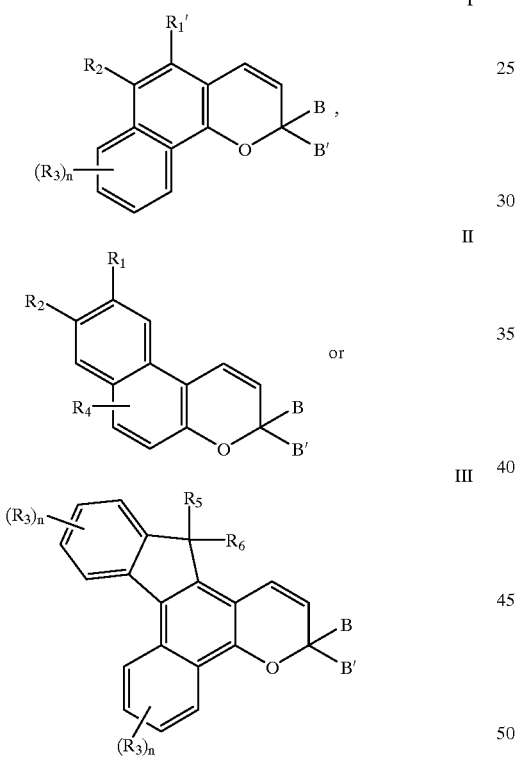

wherein, (a) $R_1$ is the group R which is represented by one of the following formulae:

—A; (1)

—D—A; (2)

—D—E—U; (3)

—D—U; (4)

—E—U; (5)

or

—U; (6)

wherein —A is represented by the following formula:

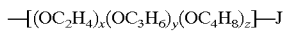

wherein —J is selected from: —OCH$_2$COOH; —OCH(CH$_3$)COOH; —OC(O)(CH$_2$)$_w$COOH; —OC$_6$H$_4$SO$_3$H; —OC$_5$H$_{10}$SO$_3$H; —OC$_4$H$_8$SO$_3$H; —OC$_3$H$_6$SO$_3$H; —OC$_2$H$_4$SO$_3$H; or —OSO$_3$H; w is an integer from 1 to 18; x, y and z are each a number between 0 and 50, and the sum of x, y and z is between 1 and 50; —D— is —C(O)— or —CH$_2$—; —E— is represented by the following formula:

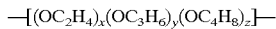

wherein x, y and z are the same as defined for —A; —U is a residue of an organic polyol having at least one hydroxyl group, or a derivative of said residue wherein one or more of said hydroxyls have been reacted to form the carboxyl, sulfo or sulfono group containing substituents —J, the group selected from (meth) acryloxy, 2-(methacryloxy)ethylcarbamyl or epoxy, or a mixture thereof provided that —U is not the same as —E—OH; or $R_1$ is hydrogen, $C_1$–$C_3$ alkyl or the group, —C(O)W, W being —OR$_7$, —N(R$_8$)R$_9$, piperidino or morpholino, wherein R$_7$ is allyl, $C_1$–$C_6$ alkyl, phenyl, mono($C_1$–$C_6$)alkyl substituted phenyl, mono($C_1$–$C_6$) alkoxy substituted phenyl, phenyl($C_1$–$C_3$)alkyl, mono ($C_1$–$C_6$)alkyl substituted phenyl($C_1$–$C_3$)alkyl, mono ($C_1$–$C_6$)alkoxy substituted phenyl($C_1$–$C_3$)alkyl, $C_1$–$C_6$ alkoxy($C_2$–$C_4$)alkyl or $C_1$–$C_6$ haloalkyl; $R_8$ and $R_9$ are each selected from the group consisting of $C_1$–$C_6$ alkyl, $C_5$–$C_7$ cycloalkyl, phenyl, mono-substituted phenyl and di-substituted phenyl, said phenyl substituents being $C_1$–$C_6$ alkyl or $C_1$–$C_6$ alkoxy, and said halo substituent being chloro or fluoro;

(b) $R_1'$ is the group R, $C_1$–$C_3$ alkyl or the group, —C(O)W, W being —OR$_7$, —N(R$_8$)R$_9$, piperidino or morpholino, wherein R$_7$ is allyl, $C_1$–$C_6$ alkyl, phenyl, mono($C_1$–$C_6$)alkyl substituted phenyl, mono($C_1$–$C_6$) alkoxy substituted phenyl, phenyl($C_1$–$C_3$)alkyl, mono ($C_1$–$C_6$)alkyl substituted phenyl($C_1$–$C_3$)alkyl, mono ($C_1$–$C_6$)alkoxy substituted phenyl($C_1$–$C_3$)alkyl, $C_1$–$C_6$ alkoxy($C_2$–$C_4$)alkyl or $C_1$–$C_6$ haloalkyl; $R_8$ and $R_9$ are each selected from the group consisting of $C_1$–$C_6$ alkyl, $C_5$–$C_7$ cycloalkyl, phenyl, mono-substituted phenyl and di-substituted phenyl, said phenyl substituents being $C_1$–$C_6$ alkyl or $C_1$–$C_6$ alkoxy, and said halo substituent being chloro or fluoro;

(c) $R_2$ is selected from the group consisting of the group R, mono-R-substituted phenyl, hydrogen, $C_1$–$C_6$ alkyl, $C_3$–$C_7$ cycloalkyl, phenyl, mono-substituted phenyl, di-substituted phenyl and the groups —OR$_{10}$ and —OC(O)R$_{10}$, wherein R$_{10}$ is $C_1$–$C_6$ alkyl, phenyl($C_1$–$C_3$) alkyl, mono($C_1$–$C_6$)alkyl substituted phenyl($C_1$–$C_3$) alkyl, mono($C_1$–$C_6$)alkoxy substituted phenyl($C_1$–$C_3$) alkyl, $C_1$–$C_6$ alkoxy($C_2$–$C_4$)alkyl, $C_3$–$C_7$ cycloalkyl or mono($C_1$–$C_4$)alkyl substituted $C_3$–$C_7$ cycloalkyl, and said phenyl substituent being $C_1$–$C_6$ alkyl or $C_1$–$C_6$ alkoxy;

(d) each $R_3$ and $R_4$ are selected from the group consisting of the group R, hydrogen, $C_1$–$C_6$ alkyl, $C_3$–$C_7$ cycloalkyl, phenyl, mono-substituted phenyl, di-substituted phenyl and the groups —OR$_{10}$ and —OC(O)R$_{10}$, wherein R$_{10}$ is $C_1$–$C_6$ alkyl, phenyl($C_1$–$C_3$)-alkyl, mono($C_1$–$C_6$)alkyl substituted phenyl($C_1$–$C_3$)

alkyl, mono(C₁–C₆)alkoxy substituted phenyl(C₁–C₃) alkyl, C₁–C₆ alkoxy(C₂–C₄)alkyl, C₃–C₇ cycloalkyl or mono(C₁–C₄)alkyl substituted C₃–C₇ cycloalkyl, and n is selected from the integers 0, 1 and 2 and said phenyl substituent being C₁–C₆ alkyl or C₁–C₆ alkoxy;

(e) R₅ and R₆ together form an oxo group, a spiro-carbocyclic ring containing 3 to 6 carbon atoms or a spiro-heterocyclic group containing 1 or 2 oxygen atoms and 3 to 6 carbon atoms including the spirocarbon atom, said spiro-carbocyclic and spiro-heterocyclic groups being annellated with 0, 1 or 2 benzene rings; or R₅ and R₆ are each the group R, hydrogen, hydroxy, C₁–C₆ alkyl, C₃–C₇ cycloalkyl, allyl, phenyl, mono-substituted phenyl, benzyl, mono-substituted benzyl, chloro, fluoro, the group, —C(O)X, wherein X is hydroxy, C₁–C₆ alkyl, C₁–C₆ alkoxy, phenyl, mono-substituted phenyl, amino, mono(C₁–C₆)alkylamino, or di(C₁–C₆)alkylamino; or R₅ and R₆ are each the group, —OR₁₁, wherein R₁₁ is C₁–C₆ alkyl, phenyl(C₁–C₃) alkyl, mono(C₁–C₆)alkyl substituted phenyl(C₁–C₃) alkyl, mono(C₁–C₆)alkoxy substituted phenyl(C₁–C₃) alkyl, C₁–C₆ alkoxy(C₂–C₄)alkyl, C₃–C₇ cycloalkyl, mono(C₁–C₄)alkyl substituted C₃–C₇ cycloalkyl, C₁–C₆ chloroalkyl, C₁–C₆ fluoroalkyl, allyl, the group, —CH(R₁₂)Y, wherein R₁₂ is hydrogen or C₁–C₃ alkyl and Y is CN, CF₃, or COOR₁₃ and R₁₃ is hydrogen or C₁–C₃ alkyl; or R₁₁ is the group, —C(O)Z, wherein Z is hydrogen, C₁–C₆ alkyl, C₁–C₆ alkoxy, the unsubstituted, mono- or di-substituted aryl groups phenyl or naphthyl, phenoxy, mono- or di-(C₁–C₆)alkyl substituted phenoxy, mono- or di-(C₁–C₆)alkoxy substituted phenoxy, amino, mono(C₁–C₆)alkylamino, di(C₁–C₆)alkylamino, phenylamino, mono- or di-(C₁–C₆)alkyl substituted phenylamino, or mono- or di-(C₁–C₆)alkoxy substituted phenylamino, each of said phenyl, benzyl and aryl group substituents being C₁–C₆ alkyl or C₁–C₆ alkoxy;

(f) B and B' are each selected from the group consisting of:
(i) mono-R-substituted phenyl;
(ii) the unsubstituted, mono-, di- and tri-substituted aryl groups, phenyl and naphthyl;
(iii) 9-julolidinyl and the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in (f)(ii) and (iii) being selected from the group consisting of hydroxy, aryl, mono(C₁–C₆)alkoxyaryl, di(C₁–C₆) alkoxyaryl, mono(C₁–C₆)alkylaryl, di(C₁–C₆) alkylaryl, chloroaryl, fluoroaryl, C₃–C₇ cycloalkylaryl, C₃–C₇ cycloalkyl, C₃–C₇ cycloalkyloxy, C₃–C₇ cycloalkyloxy(C₁–C₆)alkyl, C₃–C₇ cycloalkyloxy(C₁–C₆)alkoxy, aryl(C₁–C₆) alkyl, aryl(C₁–C₆)alkoxy, aryloxy, aryloxy(C₁–C₆) alkyl, aryloxy(C₁–C₆)alkoxy, mono- and di-(C₁–C₆) alkylaryl(C₁–C₆)alkyl, mono- and di-(C₁–C₆) alkoxyaryl(C₁–C₆)alkyl, mono- and di-(C₁–C₆) alkylaryl(C₁–C₆)alkoxy, mono- and di-(C₁–C₆) alkoxyaryl(C₁–C₆)alkoxy, amino, mono(C₁–C₆) alkylamino, di(C₁–C₆)alkylamino, diarylamino, N-(C₁–C₆)alkylpiperazino, N-arylpiperazino, aziridino, indolino, piperidino, arylpiperidino, morpholino, thiomorpholino, tetrahydroquinolino, tetrahydroisoquinolino, pyrryl, C₁–C₆ alkyl, C₁–C₆ chloroalkyl, C₁–C₆ fluoroalkyl, C₁–C₆ alkoxy, mono (C₁–C₆)alkoxy(C₁–C₄)alkyl, acryloxy, methacryloxy, bromo, chloro and fluoro, said aryl being phenyl or naphthyl;
(iv) the unsubstituted or mono-substituted groups, pyrazolyl, imidazolyl, pyridyl, pyrazolinyl, imidazolinyl, pyrrolinyl, phenothiazinyl, phenoxazinyl, phenazinyl or acridinyl, each of said substituents being selected from the group consisting of C₁–C₆ alkyl, C₁–C₄ alkoxy, phenyl, fluoro, chloro and bromo;
(v) monosubstituted phenyl, having a substituent at the para position that is a linking group, —(CH₂)ₜ— or —O—(CH₂)ₜ—, wherein t is the integer 1, 2, 3, 4, 5 or 6, connected to an aryl group, which is a member of another photochromic naphthopyran;
(vi) the groups represented by the following graphic formulae:

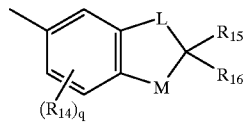 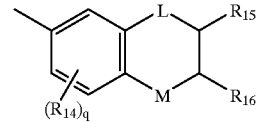

wherein L is carbon or oxygen and M is oxygen or substituted nitrogen, provided that when M is substituted nitrogen, L is carbon, said nitrogen substituents being selected from the group consisting of hydrogen, C₁–C₆ alkyl and C₂–C₆ acyl; each R₁₄ is C₁–C₆ alkyl, C₁–C₆ alkoxy, hydroxy, chloro or fluoro; R₁₅ and R₁₆ are each hydrogen or C₁–C₆ alkyl; and q is the integer 0, 1 or 2;
(vii) C₁–C₆ alkyl, C₁–C₆ chloroalkyl, C₁–C₆ fluoroalkyl, C₁–C₆ alkoxy(C₁–C₄)alkyl, C₃–C₆ cycloalkyl, mono(C₁–C₆)alkoxy(C₃–C₆)cycloalkyl, mono(C₁–C₆)alkyl(C₃–C₆)-cycloalkyl, chloro (C₃–C₆)cycloalkyl, fluoro(C₃–C₆)cycloalkyl and C₄–C₁₂ bicycloalkyl; and
(viii) the group represented by the following graphic formula:

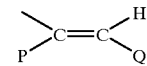

wherein P is hydrogen or C₁–C₄ alkyl and Q is selected from the unsubstituted, mono-, and di-substituted members of the group consisting of naphthyl, phenyl, furanyl and thienyl, each of said group substituents being C₁–C₄ alkyl, C₁–C₄ alkoxy, fluoro or chloro; or (g) B and B' taken together form fluoren-9-ylidene, mono-, or di-substituted fluoren-9-ylidene or a member selected from the group consisting of saturated C₃–C₁₂ spiro-monocyclic hydrocarbon rings, saturated C₇–C₁₂ spiro-bicyclic hydrocarbon rings, and saturated C₇–C₁₂ spiro-tricyclic hydrocarbon rings, each of said fluoren-9-ylidene substituents being selected from the group consisting of C₁–C₄ alkyl, C₁–C₄ alkoxy, fluoro and chloro, provided that there is at least one R group or mono-R-substituted phenyl on said naphthopyran.

2. The naphthopyran of claim 1 wherein there is one R group or mono-R-substituted phenyl on said naphthopyran.

3. The naphthopyran of claim 1 represented by graphic formula I or III, wherein:
(a) R₁' is the group R which is represented by formula: (a)(1); (a)(2); (a)(5); or (a)(6); or R₁' is the group, —C(O)W, W being —OR$_7$ or —N(R$_8$)R$_9$, wherein R$_7$ is C$_1$–C$_4$ alkyl, phenyl, mono(C$_2$–C$_4$)alkyl substituted phenyl, mono(C$_1$–C$_4$)alkoxy substituted phenyl, phenyl(C$_1$–C$_2$)alkyl, mono(C$_1$–C$_4$)alkyl substituted phenyl(C$_1$–C$_2$)alkyl, mono(C$_1$–C$_4$)alkoxy substituted phenyl(C$_1$–C$_2$)alkyl, mono(C$_1$–C$_4$)alkoxy(C$_2$–C$_3$) alkyl or C$_1$–C$_4$ haloalkyl; R$_8$ and R$_9$ are each selected from the group consisting of C$_1$–C$_4$ alkyl, C$_5$–C$_7$ cycloalkyl, phenyl, mono-substituted phenyl and di-substituted phenyl, said phenyl substituents being C$_1$–C$_4$ alkyl or C$_1$–C$_4$ alkoxy, said halo substituents being chloro or fluoro;

(b) R$_2$ is selected from the group consisting of the group R, mono-R-substituted phenyl, hydrogen, C$_1$–C$_3$ alkyl, C$_3$–C$_5$ cycloalkyl, phenyl, mono-substituted phenyl, di-substituted phenyl and the group —OR$_{10}$, wherein R$_{10}$ is C$_1$–C$_4$ alkyl, phenyl(C$_1$–C$_2$)alkyl, mono(C$_1$–C$_4$) alkyl substituted phenyl(C$_1$–C$_2$)alkyl, mono(C$_1$–C$_4$) alkoxy substituted phenyl(C$_1$–C$_2$)alkyl, C$_1$–C$_4$ alkoxy (C$_2$–C$_4$)alkyl, C$_5$–C$_7$ cycloalkyl or mono(C$_1$–C$_3$)alkyl substituted C$_5$–C$_7$ cycloalkyl and said phenyl substituents being C$_1$–C$_3$ alkyl or C$_1$–C$_3$ alkoxy;

(c) each R$_3$ is selected from the group consisting of the group R, hydrogen, C$_1$–C$_3$ alkyl, C$_3$–C$_5$ cycloalkyl, phenyl, mono-substituted phenyl, di-substituted phenyl and the group —OR$_{10}$, wherein R$_{10}$ is C$_1$–C$_4$ alkyl, phenyl(C$_1$–C$_2$)alkyl, mono(C$_1$–C$_4$)alkyl substituted phenyl(C$_1$–C$_2$)alkyl, mono(C$_1$–C$_4$)alkoxy substituted phenyl(C$_1$–C$_2$)alkyl, C$_1$–C$_4$ alkoxy(C$_2$–C$_4$)alkyl, C$_5$–C$_7$ cycloalkyl or mono(C$_1$–C$_3$)alkyl substituted C$_5$–C$_7$ cycloalkyl and said phenyl substituents being C$_1$–C$_3$ alkyl or C$_1$–C$_3$ alkoxy;

(d) R$_5$ and R$_6$ are each selected from the group consisting of the group R, hydrogen, hydroxy, C$_1$–C$_4$ alkyl, C$_3$–C$_6$ cycloalkyl, chloro, fluoro and the group, —OR$_{11}$, wherein R$_{11}$ is C$_1$–C$_3$ alkyl, phenyl(C$_1$–C$_2$)alkyl, mono (C$_1$–C$_3$)alkyl substituted phenyl(C$_1$–C$_3$)alkyl, mono (C$_1$–C$_3$)alkoxy substituted phenyl(C$_1$–C$_3$)alkyl, C$_1$–C$_3$ alkoxy(C$_2$–C$_4$)alkyl, C$_1$–C$_3$ chloroalkyl, C$_1$–C$_3$ fluoroalkyl, the group, —CH(R$_{12}$)Y, wherein R$_{12}$ is hydrogen or C$_1$–C$_2$ alkyl and Y is CN or COOR$_{13}$, and R$_{13}$ is hydrogen or C$_1$–C$_2$ alkyl, or R$_{11}$ is the group, —C(O)Z, wherein Z is hydrogen, C$_1$–C$_3$ alkyl, C$_1$–C$_3$ alkoxy, phenyl, naphthyl, mono-substituted aryl groups, phenyl or naphthyl, phenoxy, mono- or di-(C$_1$–C$_3$)alkyl substituted phenoxy, mono- or di-(C$_1$–C$_3$)alkoxy substituted phenoxy, mono(C$_1$–C$_3$) alkylamino, phenylamino, mono- or di-(C$_1$–C$_3$)alkyl substituted phenylamino, or mono- or di-(C$_1$–C$_3$) alkoxy substituted phenylamino, and said aryl substituents being C$_1$–C$_3$ alkyl or C$_1$–C$_3$ alkoxy;

(e) B and B' are each selected from the group consisting of:
   (i) mono R-substituted phenyl;
   (ii) phenyl, mono-substituted and di-substituted phenyl;
   (iii) the unsubstituted, mono- and di-substituted heteroaromatic groups furanyl, benzofuran-2-yl, thienyl, benzothien-2-yl, dibenzofuran-2-yl, and dibenzothien-2-yl, each of said phenyl and heteroaromatic substituents in (e)(ii) and (iii) being selected from the group consisting of hydroxy, aryl, arlyoxy, aryl(C$_1$–C$_3$)alkyl, amino, mono(C$_1$–C$_3$) alkylamino, di(C$_1$–C$_3$)alkylamino, N—(C$_1$–C$_3$) alkylpiperazino, indolino, piperidino, morpholino, pyrryl, C$_1$–C$_3$ alkyl, C$_1$–C$_3$ chloroalkyl, C$_1$–C$_3$ fluoroalkyl, C$_1$–C$_3$ alkoxy, mono(C$_1$–C$_3$)alkoxy (C$_1$–C$_3$)alkyl, chloro and fluoro;

(iv) the groups represented by the following graphic formulae;

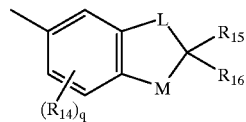 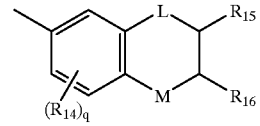

wherein L is carbon and M is oxygen, R$_{14}$ is C$_1$–C$_3$ alkyl or C$_1$–C$_3$ alkoxy; R$_{15}$ and R$_{16}$ are each hydrogen or C$_1$–C$_4$ alkyl; and q is 0 or 1;

(v) C$_1$–C$_4$ alkyl; and (vi) the group represented by the following graphic formula:

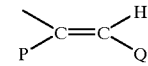

wherein P is hydrogen or methyl and Q is phenyl or mono-substituted phenyl, said phenyl substituents being C$_1$–C$_3$ alkyl, C$_1$–C$_3$ alkoxy or fluoro; or (f) B and B' taken together form fluoren-9-ylidene, mono-substituted fluoren-9-ylidene or a member selected from the group consisting of saturated C$_3$–C$_8$ spiro-monocyclic hydrocarbon rings, saturated C$_7$–C$_{10}$ spiro-bicyclic hydrocarbon rings, and saturated C$_7$–C$_{10}$ spiro-tricyclic hydrocarbon rings, said fluoren-9-ylidene substituent being selected from the group consisting of C$_1$–C$_3$ alkyl, C$_1$–C$_3$ alkoxy, fluoro and chloro.

4. The naphthopyran of claim 1 represented by graphic formula III, wherein:

(a) each R$_3$ is the group R which is represented by formula (a)(5) or (a)(6); or each R$_3$ is selected from the group consisting of hydrogen, C$_1$–C$_3$ alkyl, phenyl, mono-substituted phenyl, di-substituted phenyl and the group, OR$_{10}$, wherein R$_{10}$ is C$_1$–C$_3$ alkyl and said phenyl substituents being methyl or methoxy;

(b) R$_5$ and R$_6$ are each the group R, hydrogen, hydroxy, C$_1$–C$_4$ alkyl, or the group, —OR$_{11}$, wherein R$_{11}$ is C$_1$–C$_3$ alkyl;

(c) B and B' are each selected from the group consisting of:
   (i) mono-R-substituted phenyl;
   (ii) phenyl, mono- and di-substituted phenyl;
   (iii) the unsubstituted, mono- and di-substituted heteroaromatic groups furanyl, benzofuran-2-yl, thienyl and benzothien-2-yl, each of said phenyl and heteroaromatic substituents in (c)(ii) and (iii) being selected from the group consisting of hydroxy, C$_1$–C$_3$ alkyl, C$_1$–C$_3$ alkoxy, phenyl, indolino, fluoro and chloro; and
   (iv) the group represented by the following graphic formula:

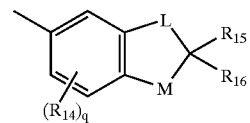

wherein L is carbon and M is oxygen, R$_{14}$ is C$_1$–C$_3$ alkyl or C$_1$–C$_3$ alkoxy; R$_{15}$ and R$_{16}$ are each hydrogen or C$_1$–C$_3$ alkyl; and q is 0 or 1; or (f) B and B' taken together form fluoren-9-ylidene, adamantylidene, bornylidene, norbornylidene, or bicyclo[3.3.1]nonan-9-ylidene.

5. A naphthopyran compound selected from the group consisting of:

(a) 3,3-di(4-methoxyphenyl)-6,11,13-trimethyl-13-(2,3-dihydroxy)propoxy-indeno[2,1-f]naphtho[1,2-b]pyran;
(b) 3,3-di(4-methoxyphenyl)-6,11,13-trimethyl-13-(2-(2-2-bis[(2-hydroxyethoxy)methyl]-3-hydroxypropyloxy)ethoxy)-indeno[2,1-f]naphtho[1,2-b]pyran;
(c) 3,3-di(4-methoxyphenyl)-6,11-dimethoxy-13-methyl-13-(2,3-dihydroxy)propoxy-indeno[2,1-f]naphtho[1,2-b]pyran;
(d) 3-phenyl-3-(4-morpholinophenyl)-13-methyl-13-(2,3-dihydroxy)propoxy-indeno[2,1-f]naphtho[1,2-b]pyran;
(e) 2,2-diphenyl-5-((2,3-dihydroxy)propoxy)carbonyl-8-methyl-[2H]-naphtho[1,2-b]pyran;
(f) 3,3-di(4-methoxyphenyl)-6,11,13-trimethyl-13-(2-(3-carboxypropanoyloxy)ethoxy)-indeno[2,1-f]naphtho[1,2-b]pyran;
(g) 3,3-di(4-methoxyphenyl)-6,11-dimethoxy-13-methyl-13-(2,3-dimethacryloxy)propoxyindeno[2,1-f]naphtho[1,2-b]pyran;
(h) 3,3-di(4-methoxyphenyl)-6,11,13-trimethyl-13-(2,3-di(2-sulfonoethyloxy))propoxy-indeno[2,1-f]naphtho[1,2-b]pyran;
(i) 3-phenyl-3-(4-morpholinophenyl)-6,11-dimethoxy-13-methyl-13-(2,3-di(4-sulfonophenoxy))propoxy-indeno[2,1-f]naphtho[1,2-b]pyran; and
(j) 3,3-di(4-methoxyphenyl)-6,11-dimethoxy-13-methyl-13-(2,3-di(epoxymethoxy))propoxy-indeno[2,1-f]naphtho[1,2-b]pyran.

6. A photochromic article comprising a polymeric organic host material selected from the group consisting of poly (methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, poly (vinylpyrrolidone), poly((meth)acrylamide), poly(dimethyl acrylamide), poly(hydroxyethyl methacrylate), poly((meth)acrylic acid), and polymers of members of the group consisting of diethylene glycol bis(allyl carbonate)monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 5.

7. A photochromic article comprising a polymeric organic host material and a photochromic amount of the naphthopyran compound of claim 1.

8. The photochromic article of claim 7 wherein the polymeric organic host material is selected from the group consisting of polyacrylates, polymethacrylates, poly ($C_1$–$C_{12}$) alkyl methacrylates, polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), poly(vinylpyrrolidone), poly((meth)acrylamide), poly(dimethyl acrylamide), poly(hydroxyethyl methacrylate), poly((meth)acrylic acid), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate)monomers, mono-functional acrylate monomers, mono-functional methacrylate monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

9. The photochromic article of claim 8 wherein the polymeric organic material is a homopolymer or copolymer of monomer(s) selected from the group consisting of acrylates, methacrylates, methyl methacrylate, ethylene glycol bis methacrylate, ethoxylated bisphenol A dimethacrylate, vinyl acetate, vinylbutyral, urethane, thiourethane, diethylene glycol bis(allyl carbonate), diethylene glycol dimethacrylate, diisopropenyl benzene, and ethoxylated trimethylol propane triacrylate.

10. The photochromic article of claim 8 wherein the photochromic compound is present in an amount of from 0.05 to 2.0 milligram per square centimeter of polymeric organic host material surface to which the photochromic substance(s) is incorporated or applied.

11. The photochromic article of claim 7 wherein said polymeric organic host material is an optical element.

12. The photochromic article of claim 11 wherein said optical element is a lens.

13. A photochromic article comprising, in combination, a solid substrate and a photochromic amount of each of (a) at least one naphthopyran compound of claim 1, and (b) at least one other organic photochromic compound having at least one activated absorption maxima within the range of between 400 and 700 nanometers.

14. A photochromic article comprising a polymerizate of an optical organic resin monomer and a photochromic amount of the naphthopyran compound of claim 1.

15. The photochromic article of claim 14 wherein the refractive index of the polymerizate is from about 1.35 to about 1.75.

16. The photochromic article of claim 14 wherein the polymerizate is an optical element.

17. The photochromic article of claim 16 wherein said optical element is an ophthalmic spectacle lens or a contact lens.

18. A photochromic article comprising, in combination, a solid substrate and on at least one surface thereof a cured coating of a coating composition having a photochromic amount of the naphthopyran compound of claim 1.

19. The photochromic article of claim 18 wherein said coating composition is selected from the group consisting of a polymeric coating composition, paint and ink.

20. The photochromic article of claim 19 wherein the substrate is selected from the group consisting of glass, masonry, textiles, ceramics, metals, wood, paper and polymeric organic material.

* * * * *

UNITED STATES PATENT AND TRADEMARK OFFICE
CERTIFICATE OF CORRECTION

PATENT NO. : 6,555,028 B2
DATED : April 29, 2003
INVENTOR(S) : Robert W. Walters and Barry Van Gemert It is certified that error appears in the above-identified patent and that said Letters Patent is hereby corrected as shown below:

Column 37,
Line 5, please delete the letter "c" and insert the letter -- C --; and
Line 16, please delete the letter "c" and insert the letter -- C --.

Signed and Sealed this

Twenty-eighth Day of September, 2004

JON W. DUDAS
*Director of the United States Patent and Trademark Office*